United States Patent
Andjelic et al.

(10) Patent No.: US 9,259,514 B2
(45) Date of Patent: Feb. 16, 2016

(54) ABSORBABLE POLYMERIC BLEND COMPOSITIONS BASED ON COPOLYMERS PREPARED FROM MONO- AND DI-FUNCTIONAL POLYMERIZATION INITIATORS, PROCESSING METHODS, AND MEDICAL DEVICES THEREFROM

(71) Applicant: Ethicon, Inc., Somerville, NJ (US)

(72) Inventors: Sasa Andjelic, Nanuet, NY (US);
Dennis D. Jamiolkowski, Long Valley, NJ (US); Brian M. Kelly, Ringoes, NJ (US); Christopher DeFelice, Springfield, NJ (US); Daniel Steiger, Basking Ridge, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 14/571,371

(22) Filed: Dec. 16, 2014

(65) Prior Publication Data
US 2015/0165096 A1 Jun. 18, 2015

Related U.S. Application Data

(60) Provisional application No. 61/917,525, filed on Dec. 18, 2013.

(51) Int. Cl.
| | |
|---|---|
| C08G 63/91 | (2006.01) |
| A61L 31/04 | (2006.01) |
| A61L 31/14 | (2006.01) |
| A61L 27/18 | (2006.01) |
| A61L 29/06 | (2006.01) |
| A61L 31/06 | (2006.01) |
| A61L 17/12 | (2006.01) |
| C08L 67/04 | (2006.01) |
| A61B 17/064 | (2006.01) |
| C08G 65/32 | (2006.01) |
| A61B 17/00 | (2006.01) |

(52) U.S. Cl.
CPC ........... *A61L 31/041* (2013.01); *A61B 17/0642* (2013.01); *A61L 17/12* (2013.01); *A61L 27/18* (2013.01); *A61L 29/06* (2013.01); *A61L 31/06* (2013.01); *A61L 31/148* (2013.01); *C08L 67/04* (2013.01); *A61B 2017/00004* (2013.01); *A61B 2017/00889* (2013.01); *A61B 2017/00893* (2013.01); *C08L 2205/025* (2013.01); *C08L 2205/03* (2013.01)

(58) Field of Classification Search
CPC ........................... A61K 9/0024; A61K 9/1647
USPC ................ 424/426, 78.38; 525/411, 413, 471
See application file for complete search history.

(56) References Cited

U.S. PATENT DOCUMENTS

| | | | |
|---|---|---|---|
| 4,052,988 A | 10/1977 | Doddi et al. | |
| 4,646,741 A | 3/1987 | Smith | |
| 5,641,501 A * | 6/1997 | Cooper et al. | 424/426 |
| 5,688,900 A * | 11/1997 | Cooper et al. | 528/301 |
| 6,794,484 B2 | 9/2004 | Newman et al. | |
| 6,831,149 B2 | 12/2004 | Newman et al. | |
| 2012/0071566 A1 | 3/2012 | Kelly et al. | |

* cited by examiner

*Primary Examiner* — Terressa Boykin
(74) *Attorney, Agent, or Firm* — E. Richard Skula

(57) ABSTRACT

Novel absorbable polymeric blends made from components wherein at least one of the components is synthesized using mixtures of mono- and di-functional initiators are disclosed. The blends have a first component that is a polylactide polymer or a copolymer of lactide and glycolide and a second component that is either poly(p-dioxanone) homopolymer, or a poly(p-dioxanone-co-glycolide) copolymer. The novel polymeric blends provide medical devices having dimensional stability. Also disclosed are novel absorbable medical devices made from these novel polymer blends, as well as novel methods of manufacture.

16 Claims, 8 Drawing Sheets

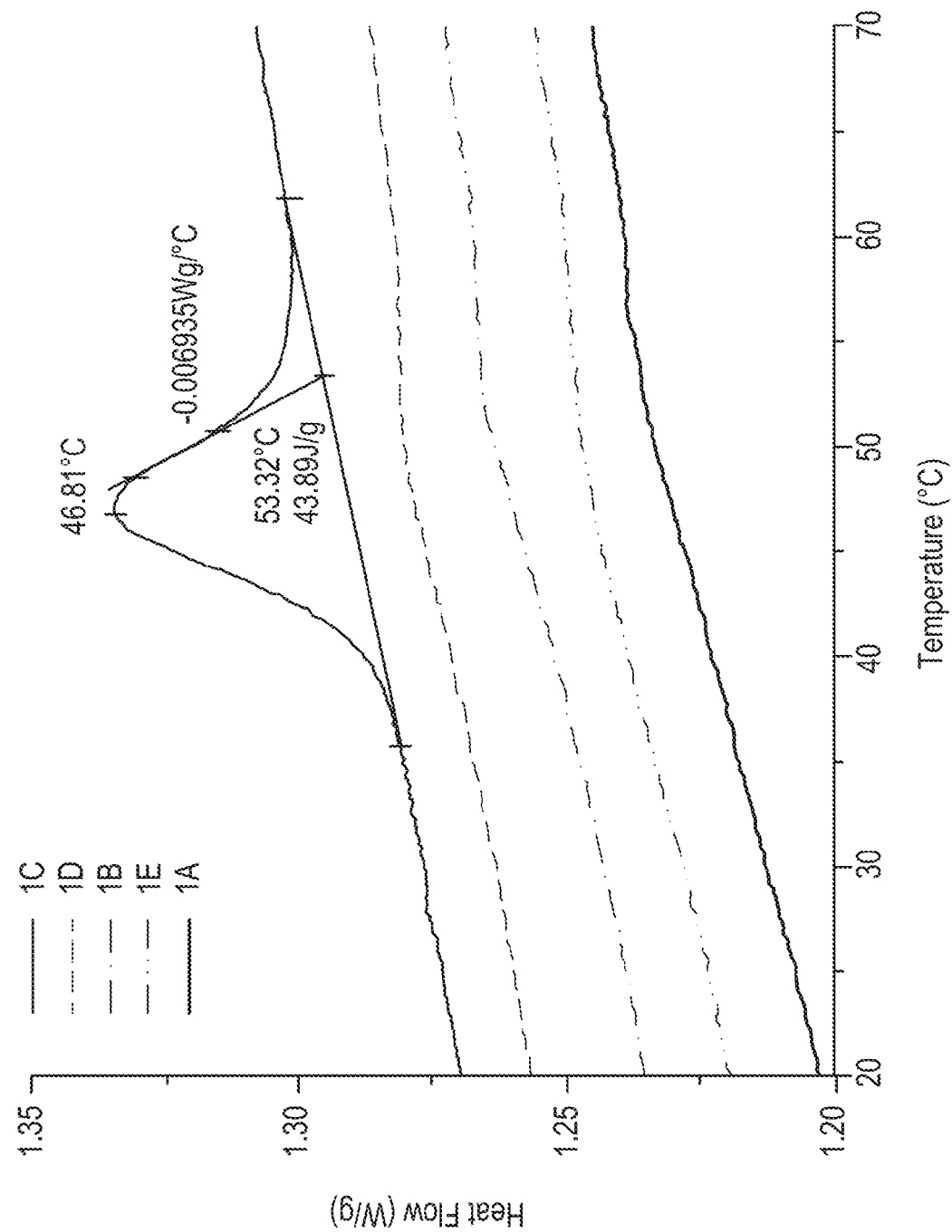

ABSORBABLE POLYMERIC BLEND COMPOSITIONS BASED ON COPOLYMERS PREPARED FROM MONO- AND DI-FUNCTIONAL POLYMERIZATION INITIATORS, PROCESSING METHODS, AND MEDICAL DEVICES THEREFROM

FIELD OF THE INVENTION

The field of art to which this invention relates is absorbable polymers, in particular, absorbable polymer blends made from absorbable polylactone copolymers prepared using a mixture of mono- and di-functional polymerization initiators, useful for manufacturing dimensionally stable implantable medical devices and medical devices prepared from such blends.

BACKGROUND OF THE INVENTION

Absorbable polymers and medical devices made from such polymers are known in the art. Conventional absorbable polymers include polylactic acid, poly(p-dioxanone), polyglycolic acid, copolymers of lactide, glycolide, p-dioxanone, trimethylene carbonate, ε-caprolactone, in various combinations, etc. The absorbable polymers are designed to have a chemistry such that the polymers breakdown in vivo and are either metabolized or otherwise broken down, for example by hydrolysis, and excreted from the patient's body. The advantages of utilizing implantable medical devices made from absorbable polymers are numerous and include, for example, eliminating the need for additional surgeries to remove an implant after it serves its function. Ideally when a "temporary presence" of the implant is desired, support can be provided until the tissue heals.

Absorbable is meant to be a generic term, which may also include bioabsorbable, resorbable, bioresorbable, degradable or biodegradable. Likewise, absorption is meant to be a generic term, which may also include bioabsorption.

The absorbable polymers used to manufacture medical devices have been on occasion polymeric blends of absorbable polymers and copolymers engineered to provide specific characteristics and properties to the manufactured medical device, including absorption rates, breaking strength retention, and dimensional stability, etc.

There are many conventional processes used to manufacture medical devices from absorbable polymers and polymer blends. The processes include injection molding, solvent casting, extrusion, machining, cutting and various combinations and equivalents. A particularly useful and common manufacturing method is thermal forming using conventional injection molding processes. It is known in this art that manufacturing processes such as thermal injection molding may result in molded parts that have inferior properties, especially, for example, unacceptable dimensional stability, mechanical properties, and retention of mechanical properties with time post-implantation. There are a number of reasons for diminished dimensional stability. They include the presence of residual stresses induced during the manufacturing process. Another reason is if at least one of the polymeric components possesses too low a glass transition temperature, especially if the polymeric component does not easily crystallize after molding.

There is on occasion a need for an absorbable material that can be fabricated into stiff dimensionally stable medical devices by conventional forming processes such as injection molding; this usually requires that the material itself possesses high stiffness. One method is the described in U.S. Patent Application Pub. No. US 2012/0071566 A1 in which poly(p-dioxanone) is blended with polylactide or a poly(lactide-co-glycolide) copolymer. The addition of the poly(p-dioxanone) however decreases the stiffness of the blend and the parts made therefrom, so that there is advantage in keeping the amount of this component to a minimum.

Therefore, there is a need in this art for novel absorbable polymer blends that can be used in thermal injection molding processes, and other conventional processes, to manufacture absorbable medical devices having superior mechanical properties such as stiffness and strength, superior breaking strength retention, excellent absorption, manufacturability, and superior dimensional stability.

It is known when using thermal injection molding processes that process conditions and design elements which reduce shear stress during cavity filling will typically help to reduce flow-induced residual stress. Likewise, those conditions that promote sufficient packing and uniform mold cooling will also typically tend to reduce thermally-induced residual stress. However, it is often very difficult, if not nearly impossible to completely eliminate residual stress in injection molded parts. Approaches that have been employed include: (1) attempting to crystallize the part while still in the mold to increase the mechanical rigidity to resist distortion; and, (2) employing resins having a high glass transition temperature ($T_g$).

This latter case describes the situation wherein chain mobility is only reached at much higher temperatures, thus protecting the part at the moderate temperatures that the part might be expected to endure during ethylene oxide (EO) sterilization, shipping, and storage. Materials possessing high glass transition temperatures may not necessarily possess other characteristics that are desirable such as absorbability. Residual stresses are believed to be the main cause of part shrinkage and warpage. Parts may warp or distort dimensionally upon ejection from the mold during the injection molding cycle, or upon exposure to elevated temperatures, encountered during normal storage or shipping of the product.

There have been attempts in the prior art to address the problem of lack of dimensional stability in medical devices thermally formed from melt blended absorbable polymers. Smith, U.S. Pat. No. 4,646,741, discloses a melt blend of a lactide/glycolide copolymer and poly(p-dioxanone) used to make surgical clips and two-piece staples. The melt blends of Smith provide molded articles possessing dimensional stability; Smith requires that the amount of poly(p-dioxanone) in the blend is greater than 25 weight percent and teaches away from lower amounts. The polymer blends of Smith have disadvantages associated with their use to manufacture medical devices, including: limited stiffness or Young's modulus, shorter retention of mechanical properties upon implantation, greater sensitivity to moisture limiting the allowable open storage time during manufacture, and, although difficult to quantify, more difficult thermal processing.

As mentioned previously, residual stresses are believed to be the main cause of part shrinkage and warpage. It is known that flow-induced residual stresses may have an effect upon a thermally molded polymeric medical device. Unstressed, long-chain polymer molecules tend to conform to a random-coil state of equilibrium at temperatures higher than the melt temperature (i.e., in a molten state). During thermal processing (e.g., injection molding), the molecules orient in the direction of flow, as the polymer is sheared and elongated. Solidification usually occurs before the polymer molecules are fully relaxed to their state of equilibrium and some molecular orientation is then locked within the molded part. This type of frozen-in, stressed state is often referred to as flow-induced residual stress. Anisotropic, non-uniform shrinkage and mechanical properties in the directions parallel and perpendicular to the direction of flow are introduced because of the stretched molecular structure.

Cooling can also result in residual stresses. For example, variation in the cooling rate from the mold wall to its center can cause thermally-induced residual stress. Furthermore, asymmetrical thermally-induced residual stress can occur if the cooling rate of the two surfaces is unbalanced. Such unbalanced cooling will result in an asymmetric tension-compression pattern across the part, causing a bending moment that tends to cause part warpage. Consequently, parts with non-uniform thickness or poorly cooled areas are prone to unbalanced cooling, and thus to residual thermal stresses. For moderately complex parts, the thermally-induced residual stress distribution is further complicated by non-uniform wall thickness, mold cooling, and mold constraints.

It should be noted that a common, conventional method of sterilization is exposure to ethylene oxide gas in a sterilization process cycle. Absorbable polymeric devices are frequently sterilized by exposure to ethylene oxide (EO) gas. EO can act as a plasticizer of lactone-based polyesters such as lactide-glycolide copolymers, and can lower the $T_g$ slightly; this may result in 'shrinkage' and/or 'warpage' of an injection-molded part, especially when exposed to temperatures higher than the $T_g$. This adds additional processing and handling challenges when using lactide-glycolide polymeric materials for absorbable medical devices. It should be noted that the EO sterilization process not only exposes the part to EO gas, it also exposes the part to elevated temperatures. Because EO can act as a plasticizer of synthetic absorbable polyesters, the problems of shrinkage and warpage and general dimensional instability are often exacerbated.

There are a number of processing methods conventionally used to reduce or eliminate shear stresses during processing. Process conditions and design elements that reduce shear stress during cavity filling will help to reduce flow-induced residual stress. Polymeric parts are often heat treated (thermally annealed) to alter their performance characteristics. The reason for the heat treatment processing is to mature the morphological development, for example crystallization and/or stress relaxation. If done successfully, the resulting part may exhibit better dimensional stability and may exhibit better mechanical strength.

Injection molded parts ejected from the injection molding machine that are not already distorted, can be cooled/quenched to room temperature and may appear to be dimensionally sound. Stresses, however, are usually still present and can drive distortion any time the polymer chains are allowed to mobilize. As previously described, this can happen with an increase in temperature or exposure to a plasticizer such as EO gas. In order to overcome this potential driving force for dimensional distortion, a number of strategies have been taken; these include (thermal) annealing.

If the part can be dimensionally constrained, thermal annealing can be employed towards two goals: one is to attempt to reduce the amount of molecular orientation in the polymer chains, also known as stress reduction; and, another is to increase the crystallinity in the part to increase the mechanical rigidity to resist distortion.

With some polymers that readily crystallize, one might be able to crystallize the part while it is still in the mold, but this is an unusual situation. Here the mold cavity not only acts to define the shape of the part, it can act to restrain the shape of the part during the crystallization process. With more-difficult-to-crystallize polymers, the cycle time becomes prohibitively long, and the injection molding process becomes impractical. Thus, the part needs to be ejected from the mold before complete polymer morphology development takes place.

As mentioned earlier, injection molded parts prepared from semi-crystalline polymers can often be annealed by thermal treatment to increase crystallinity level and complete their polymer morphology development. Often the parts must be physically constrained to avoid the distortion one is attempting to avoid. Once crystallized, the part has increased mechanical rigidity to resist distortion if exposed to normally distorting conditions. Providing suitable physical constraint is often difficult, as it is often labor intensive and economically taxing.

Annealing the ejected part without need for physical constraint is preferred; however what often happens is that the part distorts during the annealing process rendering the part unacceptable for many needs.

It is known in the industry to anneal parts to reduce molded-in-stresses by thermal relaxation. The time and temperature required to relieve stress varies, but must often be done below the $T_g$ to avoid gross distortion. Even then the results can vary greatly. It is more difficult to reduce stress levels, without causing distortion, in higher molecular weight resins. It would be relatively easy to reduce molded-in-stresses by thermal relaxation in low molecular weight, high flow polyesters, as compared to higher molecular weight polyesters.

Regarding the molecular weight of the polymer blend, higher molecular weight polymer blends usually develop higher stress levels and require longer times/higher temperatures for stress relaxation. Although this is the case, higher molecular weight is often needed to achieve high levels of mechanical properties and better biological performance. This situation often presents a problem for the device manufacturer.

In order to impart more crystallinity to increase mechanical rigidity to better resist distortion, or to reduce molecular orientation in order to lower the driving force for distortion, the parts would ideally be processed by thermal treatment (annealing) at a temperature which does not cause distortion. Unfortunately, due to the nature of the synthetic absorbable polyesters commonly employed, this treatment often needs to be above their glass transition temperature where distortion is nearly impossible to avoid.

Consider for example, polylactide homopolymeric or poly (lactide-co-glycolide) copolymeric devices. The stressed polymer chains of these injection-molded parts will tend to relax and return to their natural state ("random three-dimensional coils") when heated to or above their glass transition temperatures. This will be observed as warpage, shrinkage or general dimensional deformation. It is a general practice in the industry when producing molded polylactide-based parts, not to anneal them because of this potential deformation. These as-molded polylactide parts are of very low crystallinity, if not outright amorphous or non-crystalline, and will then tend to deform if exposed to temperatures at or above their respective glass transition temperatures. It would be advantageous to be able to anneal such parts to induce crystallinity so that they may develop the high rigidity to remain dimensionally stable under conditions normally encountered during EO sterilization, shipping, and storage.

There are medical applications that require the medical device to display sufficient column strength such as in the case of an implantable staple or a tack. Clearly, for a device having such a requirement with a smaller cross-sectional area, the polymer from which it was formed must be inherently stiff if the tack is to function properly for the intended application.

To achieve higher stiffness in a melt blend of a polylactide homopolymer or a lactide/glycolide copolymer and poly(p-dioxanone), it is necessary to minimize the amount of poly (p-dioxanone). Contrary to what Smith teaches, it has been found that dimensional stability can be achieved in parts molded from a blend of a lactide-rich copolymer and poly(p-dioxanone), in which the levels of poly(p-dioxanone) are lower than 25 weight percent. The addition of the poly(p-dioxanone), even at these low levels, enhances the ability to achieve dimensional stability in the final part. From a stiffness standpoint, however, it would be advantageous to minimize the amount of poly(p-dioxanone) in the blend.

Even though such polymer blends are known, there is a continuing need in this art for novel absorbable polymeric materials that provide a medical device with improved characteristics, including stiffness, retained strength in vivo (in situ), dimensional stability, absorbability in vivo, and manufacturability, along with a need for novel medical devices made from such polymeric materials, and novel methods of manufacturing medical devices from such polymeric materials.

SUMMARY OF THE INVENTION

The present invention is directed to an absorbable polymer blend that comprises a first absorbable polymer and a second absorbable polymer. In one aspect of the present invention the first polymer comprises at least 50 weight percent of a lactide-rich polymer comprising about 95 mole percent to about 70 mole percent polymerized lactide and about 5 mole percent to about 30 mole percent polymerized glycolide. The second polymer comprises poly(p-dioxanone). The maximum weight percent of poly(p-dioxanone) in the blend is 50 weight percent and the minimum weight percent of poly(p-dioxanone) in the blend is high enough so that the polymer blend effectively provides dimensional stability to a manufactured article. Specifically, the first absorbable polymer is synthesized using a mixture of mono- and di-functional initiators, wherein the molar ratio of mono-functional to di-functional initiator is from about 10:90 to about 90:10.

In another aspect, the present invention discloses an absorbable polymer blend that comprises a first absorbable polymer and a second absorbable polymer, in which, the first polymer comprises at least 50 weight percent of a lactide-rich polymer comprising about 100 mole percent to about 70 mole percent polymerized lactide and about 0 mole percent to about 30 mole percent polymerized glycolide. The second polymer comprises a poly(p-dioxanone-co-glycolide) copolymer, wherein the mole percent of polymerized p-dioxanone is from about 90 mole percent to about 95 mole percent, and the mole percent of polymerized glycolide is from about 5 mole percent to about 10 mole percent. The second copolymer is made utilizing a mono-functional polymerization initiator and a di-functional polymerization initiator at a mole ratio of mono-functional initiator to di-functional initiator of from about 40/60 to about 60/40. The maximum weight percent of poly(p-dioxanone-co-glycolide) copolymer in the blend is 50 weight percent and the minimum weight percent of poly(p-dioxanone-co-glycolide) copolymer in the blend is high enough so that the polymer blend effectively provides dimensional stability to a manufactured article. In addition, the first absorbable polymer may be synthesized using a mixture of mono- and di-functional initiators, in which the molar ratio of mono-functional to di-functional initiator is from about 10:90 to about 90:10.

Yet another aspect of the present invention is an absorbable polymer blend that comprises a first absorbable polymer and a second absorbable polymer, in which, the first polymer comprises at least 50 weight percent of a lactide-rich polymer comprising about 95 mole percent to about 70 mole percent polymerized lactide and about 5 mole percent to about 30 mole percent polymerized glycolide. The second polymer comprises a poly(p-dioxanone-co-glycolide) copolymer, wherein the mole percent of polymerized p-dioxanone is from about 90 mole percent to about 99 mole percent, and the mole percent of polymerized glycolide is from about 1 mole percent to about 10 mole percent. The maximum weight percent of poly(p-dioxanone-co-glycolide) copolymer in the blend is 50 weight percent and the minimum weight percent of poly(p-dioxanone-co-glycolide) copolymer in the blend is high enough so that the polymer blend effectively provides dimensional stability to a manufactured article. The first absorbable polymer is synthesized using a mixture of mono- and di-functional initiators in which the molar ratio of mono-functional to di-functional initiator is from about 10:90 to about 90:10. The second copolymer is made utilizing a mono-functional polymerization initiator and a di-functional polymerization initiator at a mole ratio of mono-functional initiator to di-functional initiator of from about 40/60 to about 60/40.

Yet another aspect of the present invention is an absorbable polymer blend that comprises a first absorbable polymer and a second absorbable polymer, in which, the first polymer comprises at least 50 weight percent of a lactide-rich polymer comprising about 95 mole percent to about 70 mole percent polymerized lactide and about 5 mole percent to about 30 mole percent polymerized glycolide. The second polymer comprises a poly(p-dioxanone-co-glycolide) copolymer, wherein the mole percent of polymerized p-dioxanone is from about 90 mole percent to about 99 mole percent, and the mole percent of polymerized glycolide is from about 1 mole percent to about 10 mole percent. The maximum weight percent of poly(p-dioxanone-co-glycolide) copolymer in the blend is 50 weight percent and the minimum weight percent of poly(p-dioxanone-co-glycolide) copolymer in the blend is high enough so that the polymer blend effectively provides dimensional stability to a manufactured article. The first absorbable polymer is synthesized using a mixture of mono- and di-functional initiators in which the molar ratio of mono-functional to di-functional initiator is from about 10:90 to about 90:10. The second copolymer is made utilizing a single initiator type, either a mono-functional polymerization initiator or a di-functional polymerization initiator.

When medical devices are manufactured from the present inventive polymer blends, the rate of crystallization during formation of the device is faster than the rate of crystallization when the polymer blends are made by a substantially similar or the same polymerization process, but utilizing either the mono-functional or the di-functional polymerization initiator alone. Thus, the present invention provides increased crystallization rates as compared to conventional processing, as taken under the same or similar measurement conditions or techniques, leading to increased dimensional stability of manufactured devices. The invention also is directed to absorbable medical devices comprising such blends.

An additional aspect of the present invention is a medical device made from the above-described novel polymer blends.

Still yet another aspect of the present invention is a method of manufacturing a medical device from the above-described polymer blends.

These and other aspects and advantages of the present invention will become more apparent from the following description and accompanying drawings.

BRIEF DESCRIPTION OF THE DRAWINGS

FIG. 13 is a graph showing non-isothermal DSC traces of copolymers 11A-11E obtained during cooling from the melt at a constant cooling rate of 0.5° C./minute; for the fast crystallizing Copolymer 11C a slope value and enthalpy of crystallization are included as well.

DETAILED DESCRIPTION OF THE INVENTION

Figure 1:
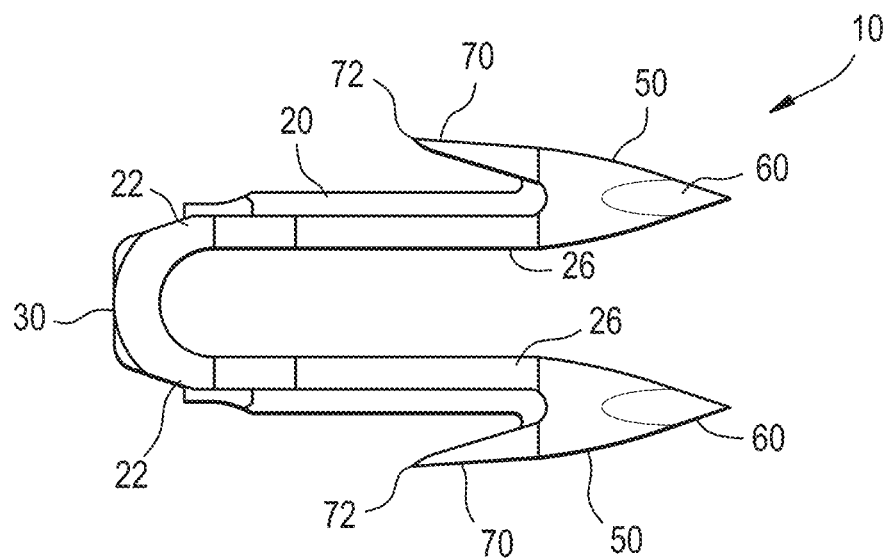
FIG. 1 is a drawing of an implantable staple or tack demonstrating the present invention, and shows a device with a small cross-sectional area.

U.S. Pat. Nos. 6,794,484 and 6,831,149 are incorporated by reference in their entirety.

The novel polymer blends of the present invention are made from a first absorbable polyester blend component and second absorbable polyester blend component, one or both of which are synthesized by using a mixture of mono-functional initiator and di-functional initiator.

Preferably, one of the blend components is poly(L(−)-lactide), poly(D(+)-lactide), the poly(L(−)-lactide)/poly(D(+)-lactide) stereocomplex, or a lactide-rich lactide/glycolide copolymer made with a mixture of mono- and di-functional initiators in which the molar ratio of mono-functional to di-functional initiator is from about 10:90 to about 90:10. Another blend component is the absorbable polymer, poly(p-dioxanone). Poly(p-dioxanone) homopolymer can be substituted in the blend with a poly(p-dioxanone-co-glycolide) copolymer, where the mole percent of polymerized p-dioxanone is from about 90 mole percent to about 95 mole percent, and the mole percent of polymerized glycolide ranges from about 5 mole percent to about 10 mole percent. This copolymer can also be made utilizing a mono-functional polymerization initiator and a di-functional polymerization initiator at a mole ratio of mono-functional initiator to di-functional initiator of from 40/60 to 60/40.

It is to be understood that in the case of the lactide-rich lactide/glycolide copolymer, the lactide is ether substantially L(−)-lactide or D(+)-lactide; specifically avoiding meso-lactide or racemic-lactide, the latter a 50/50 blend of L(−)-lactide and D(+)-lactide. It is further understood that the stereocomplex made of poly(L(−)-lactide) and poly(D(+)-lactide) may be utilized, in any proportion, with the 50/50 mixture being particularly preferred when high strength or high modulus is required. Furthermore, the lactide-rich lactide/glycolide copolymer may be a stereocomplex of a poly(L(−)-lactide-co-glycolide) and poly(D(+)-lactide-co-glycolide), in any proportion, with the 50/50 mixture again being particularly preferred. The maximum weight percent of poly(p-dioxanone) homopolymer or poly(p-dioxanone-co-glycolide) copolymer in the blend is 50 weight percent and the minimum weight percent of poly(p-dioxanone) homopolymer or poly(p-dioxanone-co-glycolide) copolymer in the blend is high enough so that the polymer blend effectively provides dimensional stability to a manufactured article.

The first blend component comprising a lactide-rich lactide/glycolide copolymer, or a stereocomplex of poly(L(−)-lactide-co-glycolide) and poly(D(+)-lactide-co-glycolide) will be manufactured in a conventional manner. A preferred synthesis method may include a ring-opening polymerization of lactide and/or glycolide monomers in a reactor outfitted with a suitable agitator, using stannous octoate at a monomer-to-catalyst mole ratio of about 50,000-200,000:1 and utilizing various ratios of mono-functional initiator, e.g. dodecanol (DD), to di-functional initiator, e.g. diethylene glycol (DEG). The monomer to initiator ratio suitable for polymers of the present invention can be in the range from about 400:1 to about 1,500:1. Preferred reaction temperatures may be selected from the range of about 150° C. to about 250° C. The absorbable polymers and copolymers useful in the practice of the present invention will have an inherent viscosity (IV) ranging typically from about 1.0 dL/g to about 4.0 dl/g, and preferably about 1.5 dL/g to about 2.5 dL/g as measured in hexafluoroisopropanol [HFIP] at a concentration of 0.1 g/dL, at a temperature of 25° C.

The second blend component can be either a poly(p-dioxanone) homopolymer or a poly(p-dioxanone-co-glycolide) copolymer made utilizing a monofunctional or a di-functional initiator alone, or utilizing a mixture of the two. Suitable monofunctional initiators include monofunctional alcohols such as dodecanol. Suitable di-functional initiators include di-functional alcohols such as diethylene glycol. In the case of poly(p-dioxanone) homopolymer, this resin can be manufactured according to processing steps described in U.S. Pat. No. 4,052,988.

When the second blend component comprises a poly(p-dioxanone-co-glycolide) copolymer, the method of manufacturing preferentially includes the utilization of a mixture of a mono-functional and a di-functional initiator as disclosed in U.S. Pat. Nos. 6,794,484 and 6,831,149, which are incorporated by reference. The fast crystallizing, low glass transition temperature (below 20° C.) copolymers of p-dioxanone and glycolide in the molar ratio of about 90/10 to about 95/5 can be conveniently made by ring-opening polymerization. The second blend component, a poly(p-dioxanone) homopolymer or a poly(p-dioxanone-co-glycolide) copolymer, useful in the practice of the present invention will have an inherent viscosity (IV) ranging typically from about 1.2 dL/g to about 2.4 dl/g, and preferably about 1.5 dL/g to about 2.0 dL/g as measured in hexafluoroisopropanol [HFIP] at a concentration of 0.1 g/dL, at a temperature of 25° C. The copolymers useful in the novel blends of the present invention will typically contain about 90 mole % to about 95 mole % of polymerized p-dioxanone, preferably about 92 mole %. The copolymers useful in the novel blends of the present invention will typically contain about 5 mole % to about 10 mole % of polymerized glycolide, preferably about 8 mole %. It is particularly preferred to use a 92/8 p-dioxanone/glycolide (PDO/Gly) block copolymer.

A preferred synthesis method for the poly(p-dioxanone) homopolymer or the poly(p-dioxanone-co-glycolide) copolymer is ring-opening polymerization of the corresponding lactone monomers, p-dioxanone with or without glycolide in a reactor outfitted with a suitable agitator, using stannous octoate at a monomer-to-catalyst mole ratio of about 20,000 to about 100,000:1.

Although the poly(p-dioxanone-co-glycolide) copolymers making up the second blend component of the present invention may be random in nature, the corresponding block copolymers are preferred.

Block copolymers of p-dioxanone and glycolide can be prepared by ring-opening polymerization in a conventional metal reactor outfitted with a suitable agitator, using a catalyst (e.g., stannous octoate) at a monomer-to-catalyst mole ratio of about 30,000:1, utilizing a 50:50 mole ratio of mono-functional initiator, dodecanol (DD), to a di-functional initiator, diethylene glycol (DEG). The monomer-to-total initiator ratio value determines the final molecular weight of the copolymer and for the purpose of the present invention 92/8 PDO/Gly copolymers can be made with the monomer-to-total initiator ratio of about 800:1 to about 900:1. It is to be understood that variation in the level of the catalyst and in the monomer-to-total initiator ratio can be made without deviating from the spirit and scope of this invention.

A polymerization process that can be used in the preparation of the PDO/Gly copolymers useful in the novel blends of the present invention is a two-step polymerization comprising a first stage homopolymerization using 100% p-dioxanone and a second stage block copolymerization with an added monomer composition of 100 mole % glycolide. The first, homopolymerization step is conducted at temperatures from about 100° C. to about 120° C. lasting for about 4-6 hours. The second, copolymerization step is typically conducted at about 130° C. to about 150° C. for additional 1-2 hours. After the second stage, unreacted p-dioxanone and glycolide monomers (typically between 10% and 20%) can be removed by a vacuum drying procedure utilizing for instance a conventional vacuum tumble drier or a conventional fluidized bed drier. In a preferred embodiment, the overall final composition of dried samples being determined by $^1$H NMR analysis, a copolymer of about 92 mole % polymerized p-dioxanone and 8 mole % polymerized glycolide is provided. In order to achieve this desired chemical composition, the initial monomer charge will be slightly higher in p-dioxanone monomer: about 94 mole % PDO and 6 mole % glycolide.

Alternatively, the discharged resin, produced and described above, may be placed in a conventional nitrogen-purged oven and heated in a solid state fashion for about 48 hours to about 80 hours at temperatures of approximately 80° C. This step may be conducted in an attempt to further increase the monomer conversion and/or increase the molecular weight of the resin. After the solid state polymerization treatment, the resin can be processed using identical procedures described for reactor-only produced resin.

The blends of the present invention either crystallize at a faster rate, or crystallize to a higher extent, or both, than their counterparts made from polymers with either a mono-functional initiator alone or a di-functional initiator alone. Crystallizing at a higher rate has advantages when melt processing the polymers of the present invention. This is especially true when fabricating, e.g., medical devices using an injection molding process. Rapid crystallization is particularly advantageous when injection molding articles from resins with low glass transition temperatures, because dimensional stability is usually achieved by crystallization in this class of materials. In the absence of crystallization, injection molded parts made from polymers possessing low glass transition temperatures also frequently display distortion and deformation upon removal from the mold because they are not able to withstand the forces exerted, however mild, during the removal process. As articles crystallize faster, injection molding cycle times may be decreased. Not only is there potential for an economic impact, i.e., decreased costs, but faster cycle times reduce the time the polymer resides in the machine at elevated temperatures reducing the amount of degradation that may occur, further improving part quality. The amount of crystallinity needed in the part prior to ejection from the mold depends on the glass transition temperature of the resin, as well as the molecular weight of the resin. The lower the glass transition temperature, the higher the level of crystallinity required. It is advantageous to have a crystallinity level of at least 10% with some synthetic absorbable polymers possessing low glass transition temperatures. In some cases, at least about 15% and preferably greater than about 25% may be necessary to provide dimensional stability.

It should be clear that the present invention may be practiced in a variety of way, still within the scope of the present invention. Table 1 below summarizes some of these ways.

TABLE 1

Various Embodiments of the Present Invention

| Case | Poly(lactide-co-glycolide) | Poly(p-dioxanone) | Polylactide | Poly(p-dioxanone-co-glycolide) copolymer |
|---|---|---|---|---|
| I | Present, Made with mixed initiators | Present | | |
| IIA | Present | | | Present, Made with mixed initiators |
| IIB | | | Present | Present, Made with mixed initiators |
| III | Present, Made with mixed initiators | | | Present, Made with mixed initiators |
| IV | Present, Made with mixed initiators | | | Present |

Problem to Be Solved I:

Many absorbable resins have rather low glass transition temperatures leading to low deflection temperatures unless the formed part is crystallized to a sufficient extent. The rate of crystallinity development during the injection molding process to form a given part is very important from an economic standpoint [parts made/hour], as cycle times increase to allow sufficient crystallization to take place in the mold. But perhaps more importantly from a performance standpoint, long cycle times will result in long residence times in the barrel leading to degradation of the resin. This degradation lowers the molecular weight of the resin resulting in lower mechanical properties and possibly faster loss of mechanical properties with time post-implantation.

It is thus desired to increase the rate of crystallization of the absorbable resin to aid the development of dimensional stability in molded parts.

A related problem is the ultimate level of crystallinity developed (as opposed to the aforementioned crystallization rate). A sufficient level of crystallinity must be developed to effectively minimize part distortion and other forms of dimensional instability such as shrinkage. The higher the molecular orientation exhibited in an injection molded part, the greater will be the driving force for distortion. With greater molecular orientation, a higher level of crystallinity is needed to resist distortion in its various forms. Additionally, synthetic absorbable polymers that have lower glass transition temperatures are more susceptible to distortion, again requiring the development of a higher level of crystallinity in the part.

Thus besides the desire to increase the rate of crystallization of the absorbable resin, it is further desired to increase the percent of crystallization developed in molded parts to increase the dimensional stability of said parts.

Solution to Problem I:

We have found in the present invention that we can provide a novel absorbable polymer blend of at least two absorbable polymers that finds utility in the manufacture of implantable medical devices that possess good dimensional stability. This is achieved by synthesizing the first absorbable polymer, a poly(lactide-co-glycolide) copolymer using a mixture of mono- and di-functional initiators, and blending it with poly(p-dioxanone). It can be also achieved by blending a first absorbable polymer selected from the group of a poly(lactide-co-glycolide) copolymer or a polylactide homopolymer with a second absorbable polymer, poly(p-dioxanone-co-glycolide) synthesized using a mixture of mono- and di-functional initiators. Alternately, one might synthesize the first and second polymers using a mixture of mono- and di-functional initiators provided that glycolide is present in the given polymer component at a minimum of 5 mole percent. One alternate embodiment of the present invention is the case in which the first absorbable polymer is a poly(lactide-co-glycolide) copolymer made using a mixture of mono- and di-functional initiators, and the second absorbable polymer is poly(p-dioxanone-co-glycolide) synthesized using either a mono-functional or a di-functional initiator.

It is to be noted that with the faster crystallization rate, and the development of higher percent crystallinity being achieved in molded parts, one might be additionally able to shift the composition of the blend to lower poly(p-dioxanone) [or poly(p-dioxanone-co-glycolide)] levels. With the reduction of the low $T_g$ polymer component, [poly(p-dioxanone) or poly(p-dioxanone-co-glycolide)], stiffness can be further increased.

Problem to Be Solved II:

At a given composition, there are instances when higher stiffness is required; this can be interpreted as requiring a higher modulus. At a given composition one might increase the percent crystallization developed in the molded part to increase the stiffness of said part. The statement of the problem then is, "Other than providing thermal treatments, how does one increase the percent crystallization level in a molded part?"

Solution to Problem II:

The present invention additionally provides a novel polymer blend suitable for making implantable medical devices that still possesses good dimensional stability in molded parts that have higher moduli than previously available absorbable blends of the same composition by virtue of selecting preferred polymerization initiators.

It should be noted that in Problem/Solution I, the poly(p-dioxanone) weight percent may be lowered—by increasing the crystallization rate, and the overall crystallinity developed, in the poly(lactide-co-glycolide) copolymer or the poly(p-dioxanone-co-glycolide) copolymer. Here with Problem II, we are considering the case wherein the blend component ratios remain invariant.

It has been found that by synthesizing the first absorbable polymer, the second absorbable polymer, or both absorbable polymers using a mixture of mono- and di-functional initiators, wherein the molar ratio of mono-functional to di-functional initiator is from about 10:90 to about 90:10, novel polymer blends can be provided suitable for making implantable medical devices that still possess good dimensional stability in molded parts, that have higher moduli than previously available absorbable blends by virtue of increased the crystallization rate, as well as increasing the overall crystallinity developed in the molded part. Additionally, the novel blends are capable of increasing the stiffness of molded parts by being able to lower the poly(p-dioxanone) weight percent without losing effective dimensional stability; this is accomplished by the poly(lactide-co-glycolide) copolymer made by mixed initiator possessing an increased crystallization rate, as well as developing a higher overall crystallinity in the molded part.

Problem to Be Solved III:

For a given modulus level, one may want to increase the rate of absorption to decrease the time the device is present in the body. This may be done by substituting a poly(p-dioxanone-co-glycolide) copolymer for the poly(p-dioxanone) homopolymeric blend component. However, the problem is that the poly(p-dioxanone-co-glycolide) copolymers made using a single initiator (mono-functional or di-functional) generally crystallize slowly thus making it difficult to develop dimensional stability.

Solution to Problem III:

In an effort to increase the absorption rate of an implanted medical device having dimensional stability, we additionally provide in the present invention a novel absorbable polymer blend that comprises a first absorbable polymer and a second absorbable polymer, in which, the first polymer comprising at least 50 weight percent of a lactide-rich polymer comprising about 100 mole percent to about 70 mole percent polymerized lactide and about 0 mole percent to about 30 mole percent polymerized glycolide. The second polymer comprising a poly(p-dioxanone-co-glycolide) copolymer, wherein the mole percent of polymerized p-dioxanone is from about 90 to about 95, and the mole percent of polymerized glycolide is from about 5 mole percent to about 10 mole percent. The second copolymer is made utilizing a mono-functional polymerization initiator and a di-functional polymerization initiator at a mole ratio of mono-functional initiator to di-functional initiator of from 40/60 to 60/40. The maximum weight percent of poly(p-dioxanone-co-glycolide) copolymer in the blend is 50 weight percent and the minimum weight percent of poly(p-dioxanone-co-glycolide) copolymer in the blend is high enough so that the polymer blend effectively provides dimensional stability to a manufactured article.

This solution begins by substituting poly(p-dioxanone-co-glycolide) copolymer for the poly(p-dioxanone) homopolymer in the previously described blends. The presence of the glycolide in the poly(p-dioxanone-co-glycolide) copolymer will increase the rate of absorption. By using mixed initiators to synthesize the poly(p-dioxanone-co-glycolide) copolymer, the rate of crystallization of this resin is increased as compared to the corresponding poly(p-dioxanone-co-glycolide) copolymer made by single imitator type, mono-functional or di-functional. This enables the preferred poly(p-dioxanone-co-glycolide) copolymer to adequately stabilize the molded part so as to undergo processing to avoid warping and dimensional instability during further in-house processing, sterilization, packaging, transportation, storage, etc.

The novel polymer blends of the present invention can be manufactured from the individual components in a variety of conventional manners using conventional processing equipment. Examples of manufacturing processes include chemical reactions of the ring-opening and polycondensation type, devolitilization and resin drying, dry blending in a tumble dryer, solution blending, extrusion melt-blending, injection molding, thermal annealing, and ethylene oxide sterilization processes. An alternate to dry blending with subsequent melt blending of the mixture can include the use of two or more feeders, preferably loss-in-weight feeders, that supply the components to be blended to an extruder; the extruder can be of the single screw or twin screw variety. Alternately, multiple extruders can be used to feed melts of the blend components, such as in co-extrusion. It should be noted that devolitilization of the resin components or of the blend to remove residual monomer and for purposes of resin drying may be accomplished by a variety of conventional means including vacuum tumble drying using an appropriate temperature scheme, or fluidized bed drying, again using an appropriate temperature scheme.

The blends of the present invention may be made by thermal processes, including conventional thermal processes. Examples of thermal processes to produce the polymer blends of the present invention include melt blending in an extruder which can include twin screw blending or single screw extrusion, co-extrusion, twin screw blending with simultaneous vented-screw vacuum devolatilization, vacuum tumble drying with thermal devolitilization, monomer removal by solvent extraction at elevated temperature, and resin annealing.

The polymer components, as well as blends of the subject invention can be sized by conventional means such as pelletization, granulation, and grinding.

A further embodiment of the present invention is directed toward feeding appropriately sized particles of the blend components directly to the hopper of the injection molding machine. In addition, one skilled in the art would appreciate that this technique can be applied to other processing methodologies, such as, but not limited to, film or fiber extrusion. Limiting the thermal history of the polymer blend components is advantageous in that it avoids the possibility of premature degradation. Additional methods of thermal processing can include a processes including injection molding, compression molding, blow molding, blown film, thermoforming, film extrusion, fiber extrusion, sheet extrusion, profile extrusion, melt blown nonwoven extrusion, co-extrusion, tube extrusion, foaming, rotomolding, calendaring, and extrusion. As noted earlier, appropriately sized particles of the blend components can be blended in the melt using these thermal processing means.

Other examples of manufacturing process equipment include chemical reactors ranging in size from about two-gallon to about seventy-five gallon capacity, process devolitilization dryers ranging from about one cubic feet to about twenty cubic feet, single and twin-screw extruders from about one inch to about three inches in diameter, and injection molders ranging from about seven to about 40 tons in size. The manufacturing process equipment will include conventional equipment in this field and equivalents thereof.

If desired, the polymer blends of the present invention may contain other conventional components and agents. The other components, additives or agents will be present to provide additional effects to the polymer blends and medical devices of the present invention including antimicrobial characteristics, controlled drug elution, radio-opacification, and osseointegration.

Such other components will be present in a sufficient amount to effectively provide for the desired effects or characteristics. Typically, the amount of the other adjuncts will be about 0.1 weight percent to about 20 weight percent. For some component types, the level may more typically be about 1 weight percent to about 10 weight percent and preferably about 2 weight percent to about 5 weight percent.

Examples of antimicrobial agents include the polychloro phenoxy phenols such as 5-chloro-2-(2,4-dichlorophenoxyl) phenol (also known as Triclosan).

Examples of radio-opacification agents include barium sulfate while examples of osseointegration agents include tricalcium phosphate.

The variety of therapeutic agents that can be used in the polymer blends of the present invention is vast. In general, the therapeutic agents may include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

Suitable polymers that may be included in the polymer blends of the present invention include: suitable biocompatible, biodegradable polymers which may be synthetic or natural polymers. Suitable synthetic biocompatible, biodegradable polymers include polymers selected from the group consisting of aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polydiglycolates, and combinations thereof. It is to be understood that inclusion of additional suitable polymers is dependent upon obtaining dimensional stability in the fabricated device.

For the purposes of this invention the above optional aliphatic polyesters include, but are not limited to, homopolymers and copolymers of lactide (which include lactic acid, D-, L- and meso-lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and blends thereof.

Suitable natural polymers include, but are not limited to collagen, elastin, hyaluronic acid, laminin, gelatin, keratin, chondroitin sulfate and decellularized tissue.

Although not preferred, the medical devices of the present invention may contain nonabsorbable polymers in addition to the absorbable polymer blends of the present invention. Examples of such devices may include but are not limited to meshes, sutures, and staples, where the properties of both the absorbable and nonabsorbable polymers are advantageous.

Suitable nonabsorbable polymers include, but are not limited to acrylics; polyamide-imide (PAI); polyaryletherketones (PEEK); polycarbonates; thermoplastic polyolefins such as polyethylene (PE), polypropylene (PP), polymethylpentene (PMP), and polybutene-1 (PB-1); polyolefin elastomers (POE) such as polyisobutylene (PIB), ethylene propylene rubber (EPR); polybutylene terephthalate (PBT); polyethylene terephthalates (PET); polyamides (PA) such as nylon 6 and nylon 66; polyvinylidene fluoride (PVDF); polyvinylidene fluoride-co-hexafluropropylene (PVDF/HFP); polymethylmethacrylate (PMMA) and combinations thereof and equivalents.

An example of a medical device that can be molded from the polymer blends of the present invention is a tissue tack 10 as seen in FIG. 1. FIG. 1 is a drawing of an implantable staple or tack demonstrating the present invention, and shows a device with a small cross-sectional area. The material of this device must be inherently stiff if the tack is to function properly for the intended application.

Figure 2:
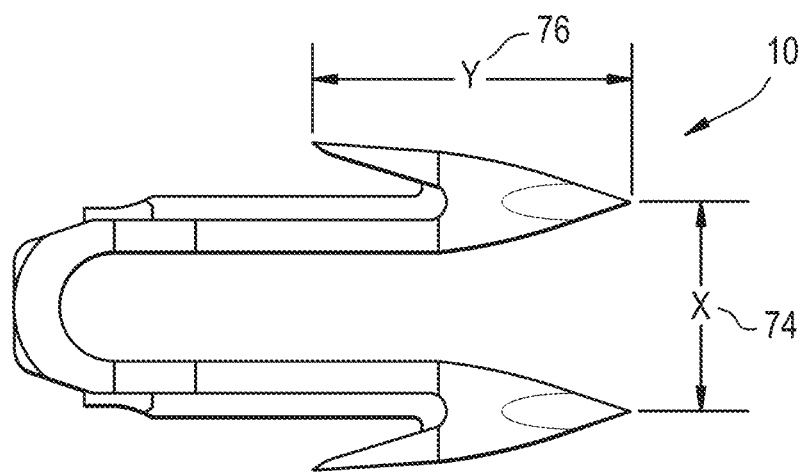
FIG. 2 is a drawing of the device of FIG. 1 showing critical dimensions of said device.

The tack 10 is seen to have two leg members 20 connected by a connecting strap member 30 at their proximal ends 22. The distal ends 26 are seen to have barb members 50 extending distally therefrom. Barb members 50 have distal tissue piercing points 60 and proximal barbs 70 having points 72. Referring to FIG. 2, barb members 50 are seen to have a length 74 shown as dimension Y. The points 60 are seen to be spaced apart by a distance 76 shown as dimension X.

Suitable tacks that can be made from the polymer blends of the present invention are also disclosed and described in commonly-assigned U.S. patent application Ser. Nos. 12/464,143; 12/464,151; 12/464,165; and, Ser. No. 12/464, 177, which are incorporated by reference.

The article chosen for evaluation was a 5 mm laparoscopic device for hernia repair; it was in the form of a staple or strap with legs and tissue holding means to the end of the legs. The device is illustrated in FIG. 2. The article was geometrically complex and was sterilized using conventional ethylene oxide sterilization processes after undergoing an annealing process. The device was used to fixate prosthetic mesh to soft tissue in both laparoscopic and open procedures.

For the device depicted in FIG. 1, the tip-to-tip distance is a critical dimension; see FIG. 2. FIG. 2 is a drawing of the device of FIG. 1 showing the critical dimensions of said device. These dimensions, if changed by lack of dimensional stability, can lead to poor performance and or failure of the device. A tip-to-tip distance of less than to 0.115 inches for the articles depicted in FIG. 1 was said to be acceptable, while a tip-to-top distance greater than or equal to 0.115 inches was said to be unacceptable and denoted as "failure mode one" or "fm1". Likewise, the length of the barb members from articles depicted in FIG. 1 were also considered critical dimensions. A barb length of less than or equal to 0.136 inches were considered unacceptable and denoted as "failure mode 2" or "fm2".

Photographic images and dimensions may be captured using a Keyence digital microscope, model VHX-600, with a magnification of 20×.

Figure 3:
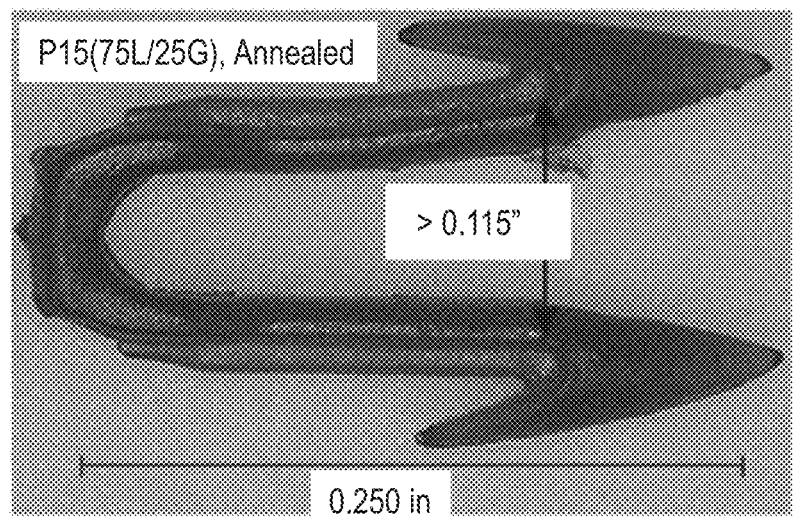
FIG. 3 is a photographic image of an injection molded tack in accordance with the device of FIG. 1 exhibiting poor dimensional stability and an unacceptable level of warping after thermal annealing.

FIG. 3 is a depiction of an injection molded tack based on the design shown in FIG. 1, prior to annealing, made from a polymer composition outside the present invention that displays unacceptable warping after annealing. FIG. 3 shows the injection molded tack after annealing—clearly warped.

Figure 4:
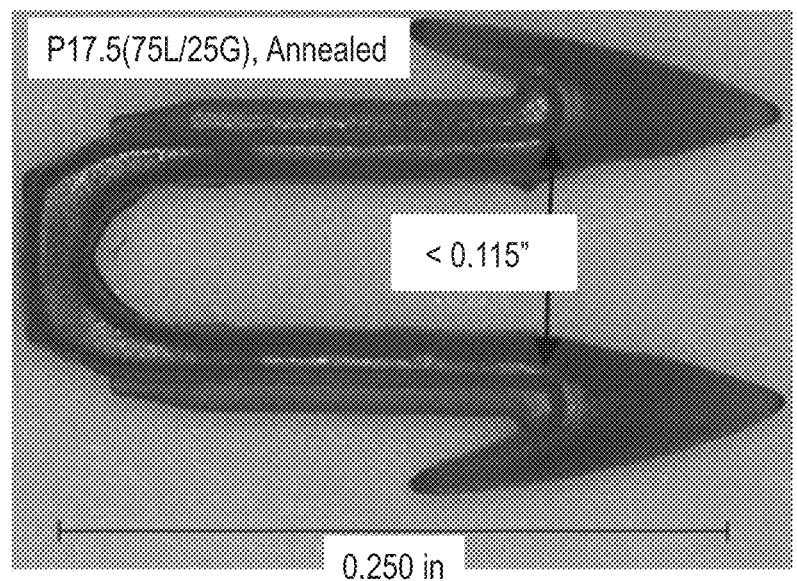
FIG. 4 is a photographic image of an injection molded tack in accordance with the device of FIG. 1 exhibiting superior dimensional stability and an acceptable level of warping after thermal annealing.

FIG. 4 is a depiction of an injection molded tack based on the design shown in FIG. 1, prior to annealing, made from a polymer composition of the present invention that displays acceptable warping after annealing. FIG. 4 shows the injection molded tack after annealing.

It is to be understood that the blend of the present invention can be used to fabricate medical devices using various melt processing techniques. As shown in some of the above examples, injection molding is one of the techniques that are applicable. It is further understood that a variety of designs may be employed utilizing the inventive blends.

Figure 5A:
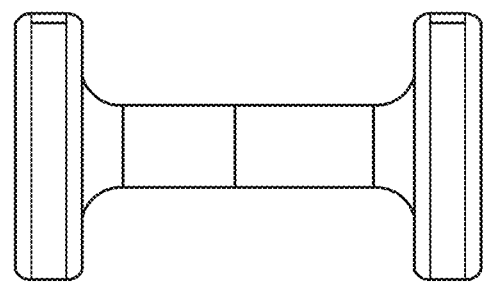
FIG. 5 is a drawing of a dumbbell test article.
Figure 5B:
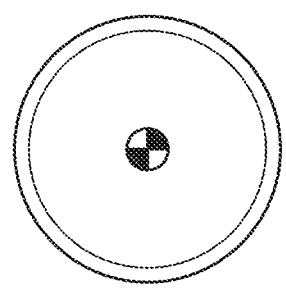
Figure 5C:
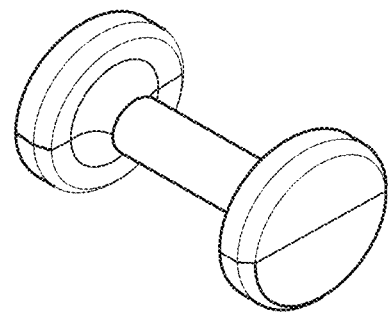

One such device that was produced was in the form of a dumbbell 0.35 inches in length with substantially disk-like termini 0.20 inches in diameter and 0.05 inches in thickness. The connection between the two disks had a substantially circular cross-section, 0.062 inches in diameter. FIG. 5 provides engineering drawings of this dumbbell device. This design is injection molded using a 85/15 lactide/glycolide copolymer as a control and a polymer blend of the present invention, specifically a melt blend of 10 weight percent poly(p-dioxanone) and 90 weight percent 85/15 (mole basis) lactide/glycolide copolymer made utilizing a mono-functional polymerization initiator, dodecanol, and a di-functional polymerization initiator, diethylene glycol, at a mole ratio of mono-functional initiator to di-functional initiator of 75/25. It should be noted that this blend composition falls outside the ranges of pending U.S. patent application Ser. No. 12/887,995, "Bioabsorbable Polymeric Compositions, Processing Methods, and Medical Devices Therefrom".

The articles, so produced, are thermally annealed without restraint at 60° C., 70° C., and 80° C. for 8, 4 and 4 hours, respectively. The devices molded from the 85/15 lactide/glycolide copolymer should show substantial shrinkage and warpage after this annealing process. The devices molded from the inventive blend should be substantially free of shrinkage and warpage after annealing.

In a preferred embodiment of the invention the injection molded part is visible in the surgical field because the polymeric blend has a violet colorant, or dye, interspersed throughout. This dye, D&C Violet No. 2, is introduced to the blend as part of the poly(p-dioxanone) homopolymer. Alternatively, colorant may be introduced to the blend as part of the lactide-based polymer. In yet another variation, the dye may be added at the time the polymer components are blended together, such as during a melt blending or dry blending process. It will be evident to one skilled in the art that the colorants may be added to the polymer compositions of the present invention in a variety of conventional manners in addition to the approaches described above. The colorants may include D&C Violet No. 2 and D&C Blue No. 6, at amounts ranging from about 0.01 weight percent to about 0.3 weight percent of the polymer blend or medical device. For surgical applications where color is not needed or desirable, undyed poly(p-dioxanone) homopolymer is used in the blend, so that the surgical article has no color.

The absorbable medical devices of the present invention that are made from the polymer blends of the present invention include but are not limited to conventional medical devices, especially implantable medical devices, including staples, tacks, clips, sutures, tissue fixation devices, mesh fixation devices, anastomosis devices, suture and bone anchors, tissue and bone screws, bone plates, prostheses, support structures, tissue augmentation devices, tissue ligating devices, patches, substrates, meshes, tissue engineering scaffolds, drug delivery devices, and stents.

The following examples are illustrative of the principles and practice of the present invention, although not limited thereto.

EXAMPLES

Example 1

Synthesis of 85/15 Poly(L(-)-Lactide-co-Glycolide)

Polymer of Normal Molecular Weight Distribution

Into a suitable, conventional 15-gallon stainless steel oil-jacketed reactor equipped with agitation, 43.778 kg of L(-)-lactide and 6.222 kg of glycolide were added along with 121.07 g of dodecanol and 9.02 mL of a 0.33M solution of stannous octoate in toluene. The reactor was closed and a purging cycle, along with agitation at a rotational speed of 12 RPM in an upward direction, was initiated. The reactor was evacuated to pressures less than 200 mTorr followed by the introduction of nitrogen gas to a pressure slightly in excess of one atmosphere. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 130° C. The vessel was held at 130° C. until the monomer was completely melted and the batch temperature reached 110° C. At this point the agitation rotation was switched to the downward direction. When the batch temperature reached 120° C., the agitator speed was reduced to 7.5 RPM, and the vessel was heated using an oil temperature of approximately 185° C., with a heat up rate of approximately 60° C. per hour, until the molten mass reached 180° C. The oil temperature was maintained at approximately 185° C. for a period of 2.5 hours.

At the end of the reaction period, the agitator speed was reduced to 5 RPM, the oil temperature was increased to 190° C., and the polymer was discharged from the vessel into suitable containers for subsequent annealing. The containers were introduced into a nitrogen annealing oven set at 105° C. for a period of approximately 6 hours; during this step the nitrogen flow into the oven was maintained to reduce degradation due to moisture.

Once this annealing cycle was complete, the polymer containers were removed from the oven and allowed to cool to room temperature. The now crystallized polymer was removed from the containers, bagged, and placed into a freezer set at approximately -20° C. for a minimum of 24 hours. The polymer was removed from the freezer and placed into a conventional Cumberland granulator fitted with a sizing screen to produce polymer granules of approximately 3/16 inches in size. The granules were then sieved to remove any "fines" and then weighed. The net weight of the ground polymer was 39.46 kg, which was then placed into a 3 cubic foot conventional Patterson—Kelley tumble dryer.

The dryer was closed and the pressure was reduced to less than 200 mTorr. Once the pressure was below 200 mTorr, tumbler rotation was activated at a rotational speed of 8-15 RPM and the batch was vacuum conditioned for a period of 10 hours. After the 10 hour vacuum conditioning, the oil temperature was set to a temperature of 120° C., for a period of 32 hours. At the end of this heating period, the batch was allowed to cool for a period of at least 4 hours, while maintaining rotation and high vacuum. The polymer was discharged from the dryer by pressurizing the vessel with nitrogen, opening the slide-gate, and allowing the polymer granules to descend into waiting vessels for long term storage.

The long term storage vessels were air tight and outfitted with valves allowing for evacuation so that the resin was stored under vacuum. The resin was characterized. It exhibited an inherent viscosity of 1.79 dL/g, as measured in hexafluoroisopropanol at 25° C. at a concentration of 0.10 g/dL. Differential Scanning calorimetry (DSC) using the heating rate of 10° C./min revealed a glass transition temperature of 59° C. and a melting transition of 150° C., with the heat of fusion about 35 J/g. Nuclear magnetic resonance (NMR) analysis confirmed that the resin was a random copolymer of polymerized L(-)-lactide and glycolide, with a composition of about 85 percent polymerized L(-)-lactide and about 15 percent polymerized glycolide on a molar basis.

Example 2

Synthesis of Poly(p-Dioxanone)

Standard Molecular Weight Polymer

Into a suitable, conventional 65-gallon stainless steel oil-jacketed reactor equipped with agitation, 164.2 kg of p-dioxanone monomer (PDO) was added along with 509 grams of dodecanol, 164 grams of D&C Violet No. 2 Dye, and 100 grams of a 0.33M solution of stannous octoate in toluene. The reactor was closed and a purging cycle, along with agitation at a rotational speed of 12 RPM in an upward direction, was initiated. The reactor was evacuated to pressures less than 500 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 100° C. The oil temperature was held at 100° C. until the batch temperature reached 50° C., at which point the agitator rotation was changed to the downward direction. When the batch temperature reached 90° C., the oil temperature was reset to 95° C. These conditions were maintained, and samples were taken from the vessel to be measured for Brookfield viscosity. When the polymer batch viscosity reached at least 110 centipoise, the batch was ready for discharge. The agitator speed was reduced to 5 RPM, and a pre-heated filter was attached to the vessel discharge port. The polymer was discharged from the vessel into suitable containers, under a nitrogen purge, covered, and transferred into a nitrogen curing oven set at 80° C. A solid state polymerization was initiated for a period of approximately 96 hours; during this step the nitrogen flow into the oven was maintained to minimize degradation due to moisture.

Once the solid state curing cycle was complete, the polymer containers were removed from the oven and allowed to cool to room temperature. The crystallized polymer was removed from the containers, and placed into a freezer set at approximately −20° C. for a minimum of 24 hours. The polymer was removed from the freezer and ground in a conventional Cumberland granulator fitted with a sizing screen to reduce the polymer granules to approximately 3/16 inches in size. The granules were then sieved to remove any "fines" and then placed into a 20 cubic foot conventional Patterson—Kelley tumble dryer.

The dryer was closed and the pressure was reduced to less than 2 mmHg. Once the pressure was below 2 mmHg, dryer rotation was activated at a rotational speed of 6 RPM with no heat for 10 hours. After the 10 hour vacuum period, the oil temperature was set to 95° C. at a heat up rate of 120° C. per hour. The oil temperature was maintained at 95° C. for a period of 32 hours. At the end of this heating period, the batch was allowed to cool for a period of at least 4 hours, while maintaining rotation and vacuum. The polymer was discharged from the dryer by pressurizing the vessel with nitrogen, opening the discharge valve, and allowing the polymer granules to descend into waiting vessels for long term storage. The storage vessels were air tight and outfitted with valves allowing for evacuation so that the resin was stored under vacuum.

The resin was characterized. It exhibited an inherent viscosity of 1.90 dL/g, as measured in hexafluoroisopropanol at 25° C. and at a concentration of 0.10 g/dL. Differential Scanning calorimetry using a heating rate of 10° C./min revealed a glass transition temperature of about −8° C. (minus eight degrees Celsius), a melting transition at about 114° C., with a heat of fusion of about 88 J/g. Nuclear magnetic resonance analysis confirmed that the resin was the homopolymer poly(p-dioxanone), with a residual monomer content less than 2 percent.

Example 3

Synthesis of Block 92/8 PDO/Gly Copolymer Used in the Present Invention

A series of PDO/Gly block copolymers were prepared by ring-opening polymerization in a clean, dry, stainless steel, oil-heated, conventional jacketed reactor equipped with a mechanical agitator using stannous octoate (total Tin 29% w/w) at a monomer-to-catalyst mole ratio of 30,000:1, utilizing 50:50 mole ratios of mono-functional initiator, dodecanol (DD), to a difunctional initiator, diethylene glycol (DEG). The monomer-to-total initiator ratio value determines the final molecular weight of the copolymer. Two 92/8 PDO/Gly copolymers will be described: a) Example 3A, with a monomer-to-total initiator ratio of 825:1, and, b) Example 3B, with a monomer-to-total initiator ratio of 900:1.

The polymerization process used in preparation of the PDO/Gly copolymers was a two-step polymerization comprising a first stage homopolymerization using 100% p-dioxanone and a second stage block copolymerization with an added monomer composition of 100 mole % glycolide. In the first stage of a typical PDO/Gly polymerization, a specified amount of p-dioxanone, stannous octoate catalyst solution (in toluene), DD and DEG (50/50 DD/DEG mole ratio), and a dye (D&C Violet No. 2, 0.04 wt. %) were charged under a nitrogen purge to a clean, dry stainless steel, oil-heated, jacketed reactor equipped with a mechanical agitator. After charging a reactor, the first step was to lower the pressure to less than one Torr for about 20 minutes, after which nitrogen gas was introduced to raise the pressure slightly over atmospheric. The evacuation/nitrogen purge process was repeated using a 25-minute vacuum-hold period. The constituents were heated under constant agitation to 110° C. and then maintained at this temperature for about four and one-half hours.

In the second stage, the temperature of the oil entering the outer jacket of the reactor was then increased to 135° C. The glycolide monomer was previously melted in the melt tank at 115° C. and transferred to the reactor containing polymerized PDO under nitrogen purge. The stirrer speed was increased to 20 RPM for the first 15 minutes of the second-stage to enhance blending of ingredients. The polymerization was continued typically for about one hour and fifteen minutes. The resulting block copolymer was discharged into aluminum or Teflon coated trays. When copolymer discharge was complete, the trays were placed in nitrogen curing oven set at room temperature to cool down overnight. The next day the resin was placed into storage bags, weighed and transferred to freezer storage. The frozen polymer was subsequently ground using 3/16" screen and then sieved using No. 18 screen sieve. The copolymer was then dried under vacuum at elevated temperature. Generally, residual glycolide monomer in all dried copolymers usually ranged from about 0.1 to about 0.2 mole percent as revealed by $^1$H NMR, while residual p-dioxanone monomer concentration usually ranged from about 0.20 to about 0.80 mole percent again as revealed by $^1$H NMR.

The drying procedure was carried out in a conventional Patterson—Kelley tumble dryer. After charging the resin, the dryer was closed, and the pressure was reduced to less than 200 mTorr. Once the pressure was below 200 mTorr, the dryer rotation was activated at a rotational speed of 10 RPM with no heat for 10 hours. After the 10 hour period, the oil jacket temperature was set to 65° C. with drying at this temperature for 4 hours. The oil temperature was again raised, this time to 75° C.; this period lasted 4 hours. The final heating period was employed at 85° C. for 24 hours. At the end of the final heating period, the batch was allowed to cool for a period of 2 hours while maintaining rotation and vacuum. The polymer was discharged from the dryer by pressurizing the vessel with nitrogen, opening the discharge valve, and allowing the polymer granules to descend into waiting vessels for long term storage. The overall final composition of dried samples, as determined by $^1$H NMR analysis, provided a copolymer of about 92 mole % polymerized p-dioxanone and about 8 mole % polymerized glycolide. In order to achieve this desired chemical composition, the initial monomer charge was slightly higher in p-dioxanone monomer: 94 mole % PDO and 6 mole % glycolide. Due to the high sensitivity of these copolymers to hydrolytic degradation, materials were stored under vacuum and tested under strict dry nitrogen conditions.

The final selected properties of dried 92/8 PDO/Gly copolymer resins that were made according to this Example are shown in Table 2.

TABLE 2

Selected Properties of Dried 92/8 PDO/Gly Copolymers of the Present Invention

| Resin ID | IV* (dL/g) | Mw** (g/mol) | MI*** (g/10 min) | Polymerized PDO (mole %) | Polymerized Gly (mole %) | PDO Monomer (mole %) | Glycolide Monomer (mole %) |
|---|---|---|---|---|---|---|---|
| Example 3A, Lower $M_w$ Resin | 1.63 | 60k | 0.212 | 91.7 | 7.5 | 0.7 | 0.2 |
| Example 3B, Higher $M_w$ Resin | 1.95 | 74k | 0.099 | 91.6 | 7.7 | 0.6 | 0.1 |

*Inherent Viscosity was determined in hexafluoroisopropanol (HFIP) solution at 25° C. at concentration of 0.1 g/dL.
**Weight Average Molecular Weight as determined by conventional GPC method
***Melt Index measurements (MT987 Extrusion Plastometer, Tinius Olsen, Willow Grove, PA, USA) were conducted at 150° C. using 6,600 g weight disc. The die diameter was 0.0260 inches, while the die length was 0.315 inches.

Alternatively, a smaller portion of the discharged resin, produced and described above, was placed in a nitrogen purged oven and heated in a solid state fashion for 72 hours at 80° C. This step was conducted in attempt to further increase the monomer conversion or/and increase the molecular weight of the resin. After the solid state polymerization treatment, the resin was ground, sieved, and dried using the same procedures described above.

Example 4

Dry Blending of 85/15 Lactide/Glycolide Copolymer with 92/8 Poly(p-dioxanone-co-glycolide) Copolymer made by Mixed Initiator Approach In the present example, a 85/15 lactide/glycolide copolymer was dried blended with the 92/8 poly(p-dioxanone-co-glycolide) copolymer made by the mixed initiators described in Example 3. The dry blends were made with a 92/8 poly(p-dioxanone-co-glycolide) copolymer made by the mixed initiators at a final blend concentration of 5, 10, and 20 weight percent. The dry blends were subsequently melt blended as described further below.

Example 5

Melt Blending of 85/15 Lactide/Glycolide Copolymer with 92/8 Poly(p-dioxanone-co-glycolide) Copolymer made by Mixed Initiator Approach Once dry blends have been produced and have been vacuum conditioned for at least three days, they can be melt-blended. The dry blends of Examples 4 were melt-blended in the following way. A conventional ZSK-30 twin-screw extruder was fitted with screws designed for melt blending utilizing dual vacuum ports for purposes of volatilizing residual monomer. The screw design contained several different types of elements, including conveying, compression, mixing and sealing elements, as would be evident to one skilled in the art. The extruder was fitted with a three-hole die plate, and a chilled water bath with water temperature set between 40° F. and 70° F. was placed near the extruder outlet. A strand pelletizer and pellet classifier was placed at the end of the water bath. The extruder temperature zones were heated to temperatures of 160° C. to 180° C., and the vacuum cold traps were set to −20° C. The pre-conditioned dry blend granules were removed from vacuum and placed in a twin-screw feed hopper under nitrogen purge. The extruder screws were set to a speed of 175 RPM to 225 RPM, and the feeder was turned on, allowing the dry blend to be fed into the extruder.

The polymer melt blend was allowed to purge through the extruder until the feed was consistent, at which point the vacuum was applied to the two vacuum ports. The polymer blend extrudate strands were fed through the water bath and into the strand pelletizer. The pelletizer cut the strands into appropriate sized pellets; it was found that pellets with a diameter of 1 mm and an approximate length of 3 mm sufficed. The pellets were then fed into the classifier. The classifier separated substantially oversized and undersized pellets from the desired size, usually a weight of about 10-15 mg per pellet. This process continued until the entire polymer dry blend was melt blended in the extruder, and formed into substantially uniform pellets. Samples were taken throughout the extrusion process and were measured for polymer characteristics such as inherent viscosity, molecular weight and composition. Once the melt-blending process was completed, the pelletized polymer was placed in polyethylene bags, weighed, and stored in a freezer below −20° C. to await devolitilization of residual monomer.

The polymer melt-blends were then placed into a conventional 3-cubic foot Patterson-Kelley dryer, which was placed under vacuum. The dryer was closed and the pressure was reduced to less than 200 mTorr. Once the pressure was below 200 mTorr, dryer rotation was activated at a rotational speed of 10 RPM with no heat for 6 hours. After the 6 hour period, the oil temperature was set to 85° C. at a heat up rate of 120° C. per hour. The oil temperature was maintained at 85° C. for a period of 12 hours. At the end of this heating period, the batch was allowed to cool for a period of at least 4 hours, while maintaining rotation and vacuum. The polymer melt-blend pellets were discharged from the dryer by pressurizing the vessel with nitrogen, opening the discharge valve, and allowing the polymer pellets to descend into waiting vessels for long term storage. The storage vessels, outfitted with valves allowing for evacuation, and being air tight, allowed the inventive resin blend to be stored under vacuum.

The inventive resin blends were characterized. Nuclear Magnetic Resonance (NMR) analysis confirmed that the blends were properly mixed in required weight amounts, with residual monomer content for all blends less than 1 percent. The blends were examined for an inherent viscosity, where samples were measured in hexafluoroisopropanol at 25° C.

and at a concentration of 0.10 g/dL. The resulting melt blend compositions were subjected to melt viscosity measurements using a melt flow index apparatus (MT987 Extrusion Plastometer, Tinius Olsen, Willow Grove, Pa., USA). The measurements were conducted at 190° C. using a 6,600 g weight disc. The die diameter was 0.0260 inches, while the die length was 0.315 inches. The results for weight average molecular weight ($M_w$) calculated by the GPC method, and Melt Flow Index (MFI), are summarized in Table 3.

TABLE 3

Melt Flow Index and Inherent Viscosity Data for Inventive Blends and a Control using Poly(p-dioxanone) Homopolymer from Example 2

| Sample ID | Comments | Wt. % of minor Poly(p-dioxanone)-based component in the blend | MFI (g/10 min) | $M_w$ (g/mole) |
|---|---|---|---|---|
| 5A | 80 wt. % 85/15 Lac/Gly Copolymer + 20% of Poly(p-dioxanone), PDS (control, non-inventive) | 20 | 0.152 | 91k |
| 5B | Blend of 80 wt. % of the copolymer of EX. 1, + 20 wt. % of the 92/8 PDO/Gly copolymer of EX. 3B | 20 | 0.075 | 85k |
| 5C | Blend of 80 wt. % of the copolymer of EX. 1, + 20 wt. % of the 92/8 PDO/Gly copolymer of EX. 3A | 20 | 0.095 | 86k |
| 5D | Blend of 90 wt. % of the copolymer of EX. 1, + 10 wt. % of the 92/8 PDO/Gly copolymer of EX. 3A | 10 | 0.059 | 109k |
| 5E | Blend of 90 wt. % of the copolymer of EX. 1, + 5 wt. % of the 92/8 PDO/Gly copolymer of EX. 3A | 5 | 0.055 | 114k |

Example 6

Calorimetric Evaluation of Inventive Blends Compositions

Differential Scanning calorimetry (DSC) was also used to investigate the thermal transitions and crystallization kinetics of blend compositions, both inventive blends of the present invention and a control. The following methods/conditions were used:
  a) First heat measurements—a 5 to 8 milligram sample of interest was quenched to −60° C. [minus 60 degrees Celsius] in a DSC pan equipped with nitrogen purge, followed by the constant heating rate scan of 10° C./min
  b) Second heat measurements—the sample of interest after melting in a DSC pan at 185° C., and followed by a rapid quench (−60° C./min) to −60° C. was then heated at the constant heating rate of 5° C./min to 185° C.

A summary of DSC results obtained on pellets of a control and blends of the present invention can be found in Table 4 below. The pellets underwent elevated temperature devolatilization that should have been sufficient to develop a nearly maximum level of crystallinity. This would be reflected in the "first heat" results. The "second heat" results reflect the inherent crystallization properties of the test samples because the thermal history would have been erased, as is well known to those skilled in the art.

TABLE 4

DSC Calorimetric Properties of a Dried Control Blend and Inventive Blends Containing 92/8 Gly/PDO Copolymer

| | | First Heat Data (10° C./min) | | | Second heat at 5° C./min | | |
|---|---|---|---|---|---|---|---|
| Sample ID | Comments | $T_g$ (L) (° C.) | $T_m$ (° C.) | $\Delta H_m$ (J/g) | $T_g$ (° C.) | $T_m$ (° C.) | $\Delta H_m$ (J/g) |
| 5A | 80 wt. % 85/15 Lac/Gly Copolymer + 20% of Poly(p-dioxanone), PDS (control, non-inventive) | 55.8 | 105/148 | 26.1 | 55.2 | 151 | 1.0 |
| 5C | Blend of 80 wt. % of the copolymer of EX. 1, + 20 wt. % of the 92/8 PDO/Gly copolymer of EX. 3A | 58.6 | 104/148 | 26.8 | 55.4 | 150 | 5.7 |
| 5D | Blend of 90 wt. % of the copolymer of EX. 1, + 10 wt. % of the 92/8 PDO/Gly copolymer of EX. 3A | 58.5 | 103/148 | 25.6 | 55.5 | 151 | 1.3 |

TABLE 4-continued

DSC Calorimetric Properties of a Dried Control Blend and Inventive Blends Containing 92/8 Gly/PDO Copolymer

| Sample ID | Comments | First Heat Data (10° C./min) | | | Second heat at 5° C./min | | |
|---|---|---|---|---|---|---|---|
| | | $T_g(L)$ (° C.) | $T_m$ (° C.) | $\Delta H_m$ (J/g) | $T_g$ (° C.) | $T_m$ (° C.) | $\Delta H_m$ (J/g) |
| 5E | Blend of 90 wt. % of the copolymer EX. 1, + 5 wt. % of the 92/8 PDO/Gly copolymer of EX. 3A | 57.2 | 104/ 147 | 25.3 | 56.5 | 152 | 1.2 |

Unexpectedly, the second heat $\Delta H_m$ values (the last column of Table 4) indicate higher crystallinity values under the given set of conditions (5° C./min heating rate) and consequently faster crystallization rates of the inventive blends over the control [Standard 85/15 Lac/Gly with 20% of PDS homopolymer, Sample 5A]. That is, $\Delta H_m$ values for the inventive blends ranged from 1.2 to 5.7 J/g versus only 1.0 J/g for the control, Sample 5A. It should be noted that the inventive blends, 5D and 5E contained only 10 wt. % and 5 wt. % of 92/8 PDO/Gly component, respectively. Surprisingly, it was observed that the presence of 92/8 PDO/Gly part in the inventive blend 5B promoted the crystallization of difficult-to-crystallize 85/15 Lac/Gly copolymer, as shown by the second heat DSC data in Table 4. To be clear, Sample 5B, made from a blend of standard 85/15 Lac/Gly with 20 weight percent of a 92/8 PDO/Gly component had a $\Delta H_m$ of 5.7 J/g as compared to a value of 1.0 J/g for the Sample 5A control. Surprisingly, the vast majority of 5.7 J/g melting endotherm originated from difficult-to-crystallize 85/15 L/G part. The control, Sample 5A was standard 85/15 Lac/Gly copolymer (Example 1) blended with 20 weight percent poly(p-dioxanone) of Example 2.

Additionally, when the samples of the inventive blends and the control were subjected to nearly optimal thermal processing conditions, thereby allowing the respective resins to crystallize to their highest practical levels, the inventive blends achieved either slightly higher crystallinity level (Sample 5C) or just slightly lower crystallinity levels (samples 5D and 5E) than the control, as evident from the $\Delta H_m$ values obtained from the first heat measurements (5$^{th}$ column of Table 4).

Example 7A

Injection Molding of Control Polymers and Blends, and Inventive Blends Containing 92/8 PDO/Gly Copolymers Into Straps and Dumbbells Injection molding is a process well known in the plastic industry. It is designed to produce parts of various shapes and sizes by melting the plastic resin, mixing and then injecting the molten resin into a suitably shaped mold. For the purpose of this invention, two injection molding shapes were explored: straps and dumbbells. These shapes are shown in FIGS. 1 and 5, respectively. After the resin is solidified, the part is generally ejected from the mold and the process continued. For the purposes of this invention, a conventional 30-ton electrically controlled injection molding machine was used. The polymers and blends of Examples 1 and 5 were processed by the injection molding machine in the following general manner.

The polymer was fed by gravity from a hopper, under nitrogen purge, into a heated barrel and allowed to melt. The polymer was moved forward in the barrel by a screw-type plunger, eventually into a heated chamber in front of the screw at the distal end of the barrel. The screw was then advanced forward in a translational motion, which forced the molten polymer through a nozzle that sat against the mold, allowing the polymers to enter a specially designed mold cavity, through a gate and runner system. The polymer was formed into the part in the mold cavity, and allowed to cool at a given temperature for a period of time. The part was then removed from the mold, or ejected, and separated from the runner.

The injection molding cycle consisted of the entire series of events during the process. It began when the mold closed, and was followed by the injection of the molten polymer into the mold cavity. Once the cavity was filled, hold pressure was maintained to compensate for material shrinkage. Next, the screw-plunger turned and retracted, feeding the next "shot" to the front of the screw. While preparing the next shot in the barrel, the part in the mold was cooled to sufficient temperature, and the mold opened and the part was ejected. The next cycle initiated upon the closing of the mold. The cycle times ranged from about 25 seconds to about 75 seconds and were based on a number of factors, including part size and material composition.

Example 7B

Annealing Molded Parts

The injection molded articles of Example 7A were then subjected to a thermal annealing cycle to mature the polymer morphology. The articles in Example 7A were annealed using an annealing fixture that supported the parts from distortion within the horizontal plane of the part. Although this annealing fixture is intended to aid in the resistance of distortion at elevated temperatures during annealing, it will not prevent dimensionally unstable parts from warping. The annealing cycle used for the articles in Example 7A was composed of three steps: 60° C. for 8 hours, 70° C. for 4 hours, and then 80° C. for 4 hours. The purpose of the 60° C. step is to further crystallize the poly(p-dioxanone) or poly(p-dioxanone-co-glycolide) phase in the blend before reaching the crystallization temperatures for the poly(lactide-co-glycolide) phase. The 70° C. step begins to crystallize the poly(lactide-co-glycolide) phase before reaching the last step in the cycle. Finally, the 80° C. step further crystallizes the poly(lactide-co-glycolide) phase. It should be noted that for a given device and given composition annealing conditions may be found that optimize certain important performance characteristics. These advantageous annealing conditions can be developed through experimentation, changing the annealing temperature and annealing duration, and measuring the response.

Once the injection parts of Example 7A were annealed, they were identified as the annealed parts of Example 7B.

Example 8

Calorimetric Properties of Annealed Dumbbells calorimetric data was obtained utilizing Differential Scanning calorimetry (DSC), at a heating rate of 10° C./min with a sample weight of 5 mg to 8 mg on a number of annealed dumbbells (DB). These include samples based on: a control blend of 80 weight percent 85/15 L/G copolymer and 20 weight percent PDS [Sample DB 8A]; the neat 85/15 L/G copolymer of Example 1 [DB 8B]; the inventive blend of 80 weight percent 85/15 L/G copolymer and 20 weight percent 92/8 PDO/Gly copolymer of Example 3A [DB 8C], as well as the inventive blend of 80 weight percent 85/15 L/G copolymer and 20 weight percent 92/8 PDO/Gly copolymer of Example 3B [DB 8D]. It should be noted that annealed dumbbells DB 8C and DB 8D are identical in composition, but differ in molecular weight; DB 8C is slightly lower in molecular weight than DB 8D. The DSC results obtained on annealed dumbbells (center section) made from these various blends are summarized in Table 5 below.

TABLE 5

Calorimetric (DSC) Properties of Annealed[1] Control Dumbbell and Corresponding Dumbbells Made from Inventive 92/8 PDO/Gly Copolymer Containing Blends

| Sample ID | Comments | First Heat Data (10° C./min) | | | |
|---|---|---|---|---|---|
| | | $T_g$ [P] (° C.) | $T_g$ [L] (° C.) | $T_m$ (° C.) | $\Delta H_m$ (J/g) |
| DB 8A | Annealed dumbbell piece from the blend 5A containing 20 wt. % PDS (control) | −19.6 | 46.3 | 102/ 147 | 28.9 |
| DB 8B | Annealed dumbbell piece from 85/15 L/G copolymer of EX. 1 | NA | 53.5 | 148 | 26.5 |
| DB 8C | Annealed piece from the inventive blend of EX. 1 and EX. 3A, containing 20 wt. % of 92/8 PDO/Gly copolymer | −3.6 | 54.2 | 102/ 147 | 35.0 |
| DB 8D | Annealed piece from the inventive blend of EX. 1 and EX. 3B, containing 20 wt. % of 92/8 PDO/Gly copolymer | −2.3 | 56.3 | 101/ 148 | 34.0 |

[1]Annealing conditions: 60° C. for 8 hrs, followed by 70° C. for 4 hrs, followed by 80° C. for 4 hrs The DSC results shown in Table 5 above allow for the following conclusions. The glass transition temperature, $T_g$, of poly(p-dioxanone) [AKA PDS] or poly(p-dioxanone-co-glycolide) copolymer was identified in those blends, which is indicative of phase separated morphology. The melting behavior resulted in the observation of two melting transition temperatures, $T_{m1}$ and $T_{m2}$, although overlapping, in those articles based on blends of 85/15 L/G copolymer and PDS or poly(p-dioxanone-co-glycolide) copolymer. One of these melting transitions temperatures corresponded to the homopolymer poly(p-dioxanone, or to the poly(p-dioxanone-co-glycolide) copolymer and the other corresponded to the L/G copolymer. In the case of the control dumbbell (DB 8A), the PDS-based melting was observed at 102° C., while the L/G-based melting was at 147° C. In the case of the dumbbells made from the inventive blends (8C and 8D) the poly (p-dioxanone-co-glycolide) copolymer-based meltings ranged from 101° C. to 102° C., while the L/G-based meltings ranged from 147° C. to 148° C. The presence of these two endotherms and the fact that they remain fairly invariant with regard to temperature even though the relative amounts of the blend components vary is further indicative of the phase separated morphology. The combined heats of melting, $\Delta H_m$, of the two melting endotherms is reported in the last column of Table 5. It is well established that that the heat of fusion is proportional to the crystallinity level of the part. We can thus model the crystallinity level by following the $\Delta H_m$.

It is noted that all the annealed molded dumbbells prepared from the resins based on inventive blends of L/G copolymer and 92/8 poly(p-dioxanone-co-glycolide) copolymers of Examples 3A and 3B listed in Table 5 exhibited much higher $\Delta H_m$ values when compared to the L/G copolymer alone [Sample DB 8B] and compared to the non-inventive, control blend [Sample DB 8A]. These higher $\Delta H_m$ values imply an expected higher crystallinity levels. Higher crystallinity levels in dumbbells can lead to stronger and stiffer devices as will be shown in Example 9 below.

Example 9

Tensile Properties of Annealed Dumbbells Made From a Control Blend and a Series of Inventive Blend Compositions Made by Mixed Initiators Annealed test specimens in the form of dumbbells made by injection molding as described in Example 7A and 7B (specifically Samples DB 8A, DB 8C, and DB 8D) were examined with respect to mechanical properties.

The annealed dumbbells were tested utilizing a conventional mechanical tester, Instron Model 5544 (Norwood, Mass., USA), using a 100 lbs. load cell. All instruments were within calibration at the time of testing. The specimens were loaded in tension at a rate of 0.5 in/min until fracture. The maximum force was recorded as the tensile strength of the specimen. The Young's Modulus was calculated as the slope of the line linking two points located on the linear region of the force-extension curve of the test specimen. The following formula was utilized:

$$E = (\Delta F/A_0)/(\Delta L/L_0)$$

where E is the calculated Young's Modulus, $\Delta F$ is the change in force measured at the selected points, $A_0$ is the initial cross-sectional area of the specimen, $\Delta L$ is the change in cross-head displacement at selected points and $L_0$ is the gage length of the specimen. The initial cross-sectional area and the gage length considered in the calculations were $2.83 \times 10^{-3}$ in$^2$ and 0.25 inches, respectively. The summary of data is given in Table 6.

TABLE 6

Tensile Strength and Young's Modulus (Stiffness) Data for Selected Dumbbell Samples Made from Mixed Initiators Blends of the Present Invention and a Control

| Sample ID | Comments | Max. Load (lbf) | Max. Load SDEV | Young's Modulus (kpsi) | YM SDEV |
|---|---|---|---|---|---|
| DB 8A | Annealed control piece from prior art, based on a blend of 80 Wt. % 85/15 L/G copolymer + 20 Wt. % PDS | 26.30 | 1.68 | 130.3 | 4.81 |
| DB 8C | Annealed piece from the inventive blend of EX. 1 and EX. 3A, containing 20 wt. % of lower molecular weight 92/8 PDO/Gly copolymer | 28.81 | 0.81 | 133.1 | 6.35 |
| DB 8D | Annealed piece from the inventive blend of EX. 1 and EX. 3B, containing 20 wt. % of higher molecular weight 92/8 PDO/Gly copolymer | 30.10 | 0.40 | 139.4 | 4.11 |

The data of Table 6 above show that for the same amount of minor component, either PDS or 92/8 PDO/Gly copolymer (20%), annealed dumbbells made from 92/8 PDO/Gly copolymer containing blends are stronger and stiffer than the control blend made with the same overall composition, but with PDS homopolymer. This is due to higher crystallinity levels of annealed dumbbells made from the inventive blends, as evident from Table 6 (Samples DB 8C and 8D).

Example 10

Dimensional Stability

The injection molded articles of Examples 7A and 7B [that is molded articles before and after annealing] in the form of straps (AKA tacks or staples; see FIGS. 1 and 2) were tested for dimensional stability. The dimensions of the molded articles were measured prior to annealing and after annealing; additionally, photographic images were taken [see FIG. 6 to FIG. 11]. Although it is not expected to have all dimensions match exactly, it is clear that certain dimensions are critical to the functioning of the device. In some of the cases unacceptable levels of distortion were found; the inventive articles made from the inventive blends, however, displayed acceptable dimensional stability.

The test articles of Examples 7A and 7B in the form of straps are geometrically complex and have a number of critical dimensions. For instance, if the legs of the molded article distort excessively, the ability of the device to penetrate and hold tissue will be reduced. Likewise, if the barbs of the molded article were to shrink significantly, functionality would be reduced because of diminished ability to hold tissue. Every design will have its own critical dimensions. It is believed that the design of the straps of Examples 7A and 7B is representative of a demanding device regarding dimensional stability; this is felt in part because of geometric complexity and because of the expected high shear generated during molding of these small parts. That is, the fine part size will tend to increase molecular orientation during injection molding leading to an increased driving force for distortion of the ejected part [that is the part after removal from the mold cavity] at elevated temperatures as seen in annealing, and/or sterilization, and/or storage. Parts were evaluated and characterized in a "pass/fail" manner. Disposition of the molded articles were based on gross warping effects, of which an article was considered to have passed if excessive distortion was not evident. Likewise, if excessive distortion was evident, the part was said to have failed. Inherently, all injection molded articles have some degree of residual stress after molding, so parts that display tolerable levels of distortion are said to have passed the dimensional stability test. For the articles of Examples 7A and 7B, the tip-to-tip distance is a critical dimension; see FIG. 1.

FIG. 2 is a drawing of the device of FIG. 1 showing the critical dimensions of said device. These dimensions, if changed by lack of dimensional stability, can lead to poor performance and or a failure of the device. A tip-to-tip distance of less than 0.115 inches for the strap articles of Examples 7A and 7B was said to be acceptable, while a tip-to-top distance greater than or equal to 0.115 inches was said to be unacceptable and denoted as "failure mode one" or "fm1". Likewise, the lengths of the barb members from the straps of Examples 7A and 7B were also considered critical dimensions. A barb length of less than or equal to 0.136 inches was considered unacceptable and denoted as "failure mode 2" or "fm2". The photographic images and dimensions were captured using a Keyence digital microscope, model VHX-600, with a magnification of 20×. A summary of the test results is shown in Table 7 below.

TABLE 7

Calorimetric (DSC) Properties of Annealed[1] Control Straps and Corresponding Straps Made from Inventive Blends Containing 92/8 PDO/Gly Copolymer Blends.

| Sample ID | Comments | First Heat Data (10° C./min) | | | | Dimensional stability? |
|---|---|---|---|---|---|---|
| | | $T_{g1}^2$ (° C.) | $T_{g2}^2$ (° C.) | $T_m^3$ (° C.) | $\Delta H_m$ (J/g) | |
| STR 10-1 | Annealed control strap from 85/15 L/G copolymer of EX. 1 | Molding parts failed to hold its shape, with sticking issues during injection molding and various distortions | | | | |
| STR 10-2 | Annealed control strap from prior art, based on a blend of 80 Wt. % 85/15 L/G copolymer + 20 Wt. % PDS | −9.8 | 52.6 | 103/ 148 | 33.6 | YES |
| STR 10-3 | Annealed strap from the inventive blend of EX. 1 and EX. 3A, containing 20 wt. % of lower molecular weight 92/8 PDO/Gly copolymer | −0.5 | 56.8 | 101/ 146 | 35.5 | YES |
| STR 10-4 | Annealed strap from the inventive blend of EX. 1 and EX. 3A, containing 10 wt.% of lower molecular weight 92/8 PDO/Gly copolymer | −4.1 | 58.8 | 101/ 149 | 29.8 | NO |
| STR 10-5 | Annealed strap from the inventive blend of EX. 1 and EX. 3A, containing 5 wt. % of lower | −7.4 | 58.2 | 102/ 148 | 25.2 | NO |

TABLE 7-continued

Calorimetric (DSC) Properties of Annealed[1] Control Straps and Corresponding Straps Made from Inventive Blends Containing 92/8 PDO/Gly Copolymer Blends.

| | | First Heat Data (10° C./min) | | | | |
|---|---|---|---|---|---|---|
| Sample ID | Comments | $T_{g1}^2$ (°C.) | $T_{g2}^2$ (°C.) | $T_m^3$ (°C.) | $\Delta H_m$ (J/g) | Dimensional stability? |
| | molecular weight 92/8 PDO/Gly copolymer | | | | | |

[1]Analysis conducted on the crown portion of an annealed molded strap. The annealing conditions employed were 60° C. for 8 hours followed by 70° C. for 4 hours followed by 80° C. for 4 hours.
[2]$T_{g1}$ refers to the glass transition values of the poly(p-dioxanone) homopolymer or the poly(p-dioxanone-co-glycolide) blend component while $T_{g2}$ refers to the glass transition values of the lactide-glycolide copolymer blend component.
[3]Listed herein are two values; the first is represents the melting point of PDS or 92/8 PDO/Gly-based blend component and the second value represents the melting point observed for the lactide-based blend component.

In Table 7 above, the calorimetric properties of annealed straps of Examples 7B are provided along with the results of dimensional stability testing. The calorimetric data is a result of DSC (first heat) testing as described earlier in this application. The "first heat" DSC measurements were used to calculate the heats of fusion, $\Delta H_m$ (J/g), of the annealed straps [see Example 7B]. These values are directly proportional to the relative crystallinity level present in the test articles.

The annealed articles shown in Table 7 are of three varieties. In one case, the annealed straps are based on blends in which the blend components are with minor, poly(p-dioxanone) component, [Sample STR 10-2]. In a second case, the annealed straps are based on a lactide/glycolide copolymer of Example 1 only, [STR 10-1]. The third variety represents a series of blends containing different amount of 92/8 poly(p-dioxanone-co-glycolide) copolymer [Samples STR 10-3, STR 10-4, and STR 10-5]; the level of the minor blend component, 92/8 poly(p-dioxanone-co-glycolide) copolymer, was 5, 10 or 20 weight percent.

A dimensional stability examination of the strap articles of Example STR 10-1 was performed. These articles are based on an 85/15 lactide/Glycolide copolymer only. The strap articles of Sample STR 10-1 acted as a control group—Control 1. Although the articles exhibited crystallinity after annealing, the molded parts failed to hold shape during this process; they were dimensionally unstable with significant distortions being observed.

The injection molded straps of Example STR 10-2 are based on the prior art blend of 80% 85/15 L/G copolymer and 20% PDS and represent a second control group—Control 2. As expected, these articles exhibited dimensional stability. Dimensional stability is provided by the presence of 20 weight percent of poly(p-dioxanone). The annealed straps of Example STR 10-2 exhibited a $\Delta H_m$ of 33.6 J/g, indicative of a significant level of crystallinity. The presence of the poly(p-dioxanone) blend component does, however, decrease the stiffness of the article. Minimizing the amount of poly(p-dioxanone) present in the blend would lead to stiffer articles which in certain applications would be advantageous. To achieve dimensional stability in finely detailed molded articles, however, it has been shown in the prior art that a minimum of about 12.4 weight percent of poly(p-dioxanone) is required.

The injection molded straps of Samples STR 10-3 to STR 10-5 are based on blends containing 92/8 poly(p-dioxanone-co-glycolide) copolymer. Specifically, these were blends made from 85/15 L/G copolymer of standard molecular weight ranging from 80 wt. % to 95 wt. %, blended with 92/8 poly(p-dioxanone-co-glycolide) copolymer, in which the latter component is present at 5, 10 and 20 weight percent, respectively. The inventive articles of Sample STR 10-3 exhibited dimensional stability; this corresponds to 92/8 poly(p-dioxanone-co-glycolide) copolymer being present at the 20 weight percent level. Based on the calorimetric data of Table 6, the annealed strap made from this inventive blend, exhibited relatively high levels of crystallinity, a $\Delta H_m$ of 35.5 J/g. On the other hand, the annealed straps of Samples STR 10-4 and STR 10-5, made with only 10 and 5 weight percent 92/8 poly(p-dioxanone-co-glycolide) copolymer exhibited lower crystallinity, a $\Delta H_m$ of 29.8 J/g, and 25.2 J/g, respectively. These straps (tacks) did not exhibit dimensional stability as noted in Table 7. Dimensional stability was found to be dependent on the $\Delta H_m$ (or crystallinity) of the article; when the annealed article exhibited a $\Delta H_m$ of greater than about 31 J/g, the article tended to be dimensionally stable.

Further evidence of dimensional stability or instability is presented in the photographs of FIG. 6 to FIG. 11 where the injection molded straps made from the composition of Examples 7A and 7B having a 92/8 poly(p-dioxanone-co-glycolide) copolymer blend component at 5, 10 or 20 weight percent are depicted.

Figure 6:
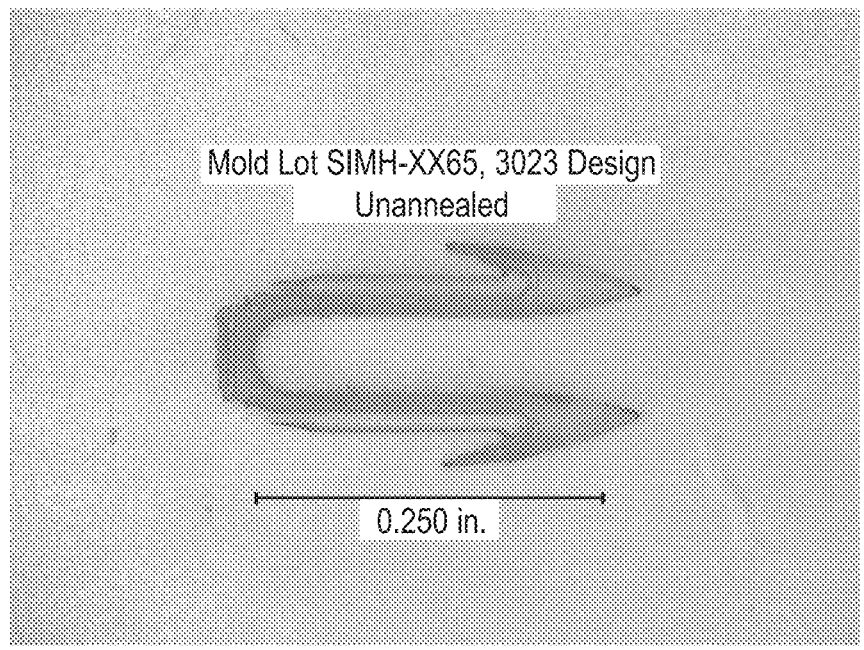
FIG. 6 is a photographic image of an injection molded tack of Sample STR 10-5 prior to annealing made from the polymer composition of Example 7A having 5 weight percent 92/8 poly(p-dioxanone-co-glycolide).
Figure 7:
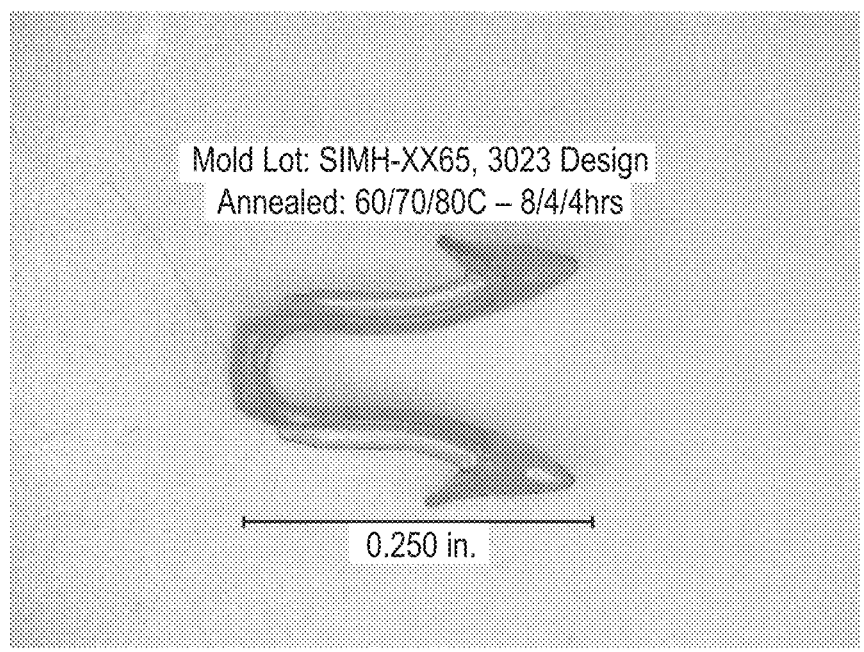
FIG. 7 is a photographic image of an injection molded tack of Sample STR 10-5 after annealing, made from the polymer composition of Example 7B having 5 weight percent 92/8 poly(p-dioxanone-co-glycolide), said injection molded tack exhibiting unacceptable warping after annealing.

FIG. 6 is a photographic image of an injection molded tack of Sample STR 10-5 prior to annealing made from the polymer composition of Example 7A having 5 weight percent 92/8 poly(p-dioxanone-co-glycolide) copolymer; FIG. 7 is a photographic image of an injection molded tack of Sample STR 10-5 after annealing made from the polymer composition of Example 7B having 5 weight percent 92/8 poly(p-dioxanone-co-glycolide) copolymer; these injection molded tacks exhibited unacceptable warping after annealing.

Figure 8:
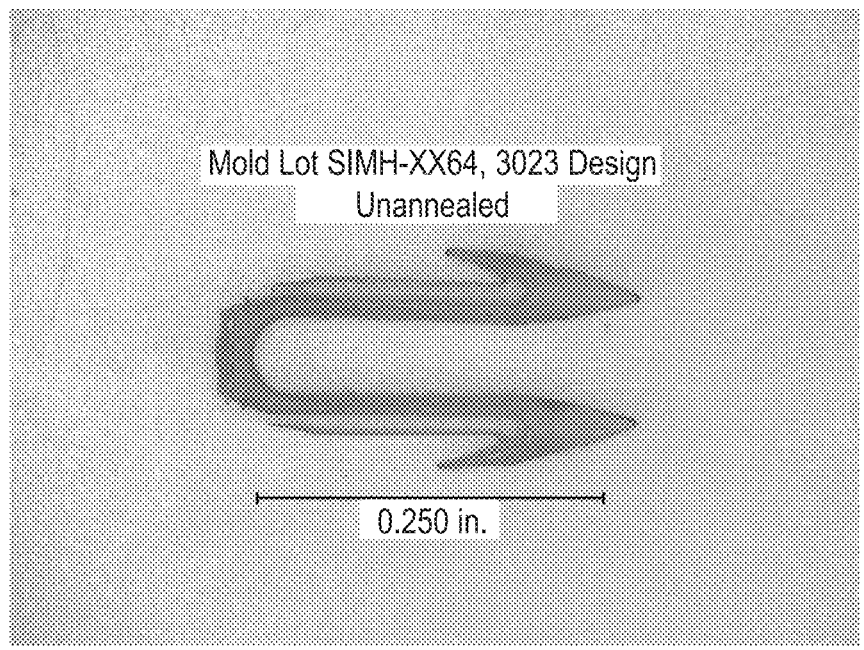
FIG. 8 is a photographic image of an injection molded tack of Sample STR 10-4 prior to annealing made from the polymer composition of Example 7A having 10 weight percent 92/8 poly(p-dioxanone-co-glycolide).
Figure 9:
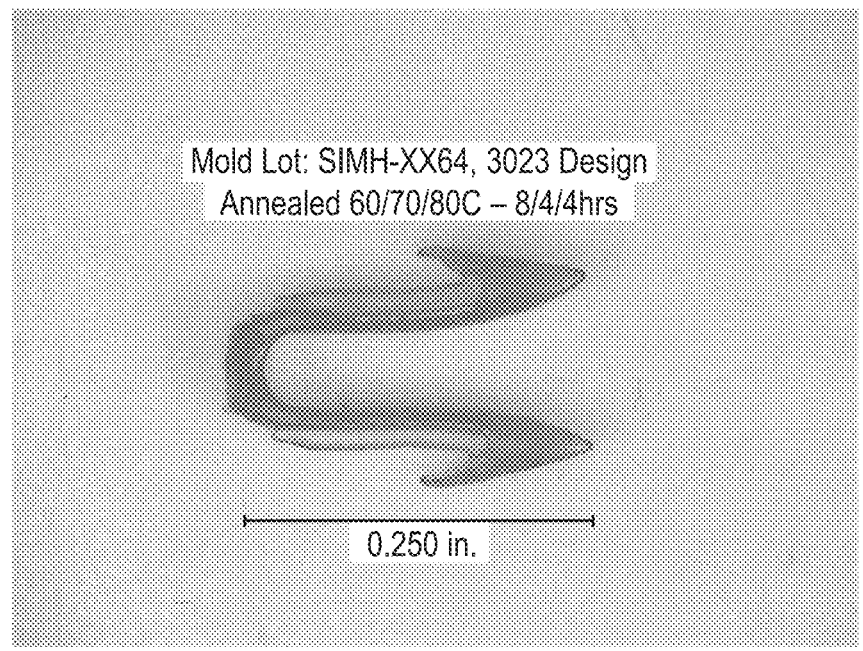
FIG. 9 is a photographic image of an injection molded tack of Sample STR 10-4 after annealing, made from the polymer composition of Example 7B having 10 weight percent 92/8 poly(p-dioxanone-co-glycolide), said injection molded tack exhibiting unacceptable warping after annealing.

FIG. 8 is a photographic image of an injection molded tack of Sample STR 10-4 prior to annealing made from the polymer composition of Example 7A having 10 weight percent 92/8 poly(p-dioxanone-co-glycolide) copolymer; FIG. 9 is a photographic image of an injection molded tack of Sample STR 10-4 after annealing made from the polymer composition of Example 7B having 10 weight percent 92/8 poly(p-dioxanone-co-glycolide) copolymer; these injection molded tacks also exhibited unacceptable warping after annealing. However, in comparing the photographs of FIGS. 6 to 9, it is observed that the level of distortion of tack STR 10-4 after annealing was much less than what is seen in the tack based on only 5 weight percent 92/8 PDO/Gly copolymer. The photographs suggest that slightly more than 10 weight percent of 92/8 PDO/Gly copolymer is needed in a blend to ensure dimensional stability.

Figure 10:
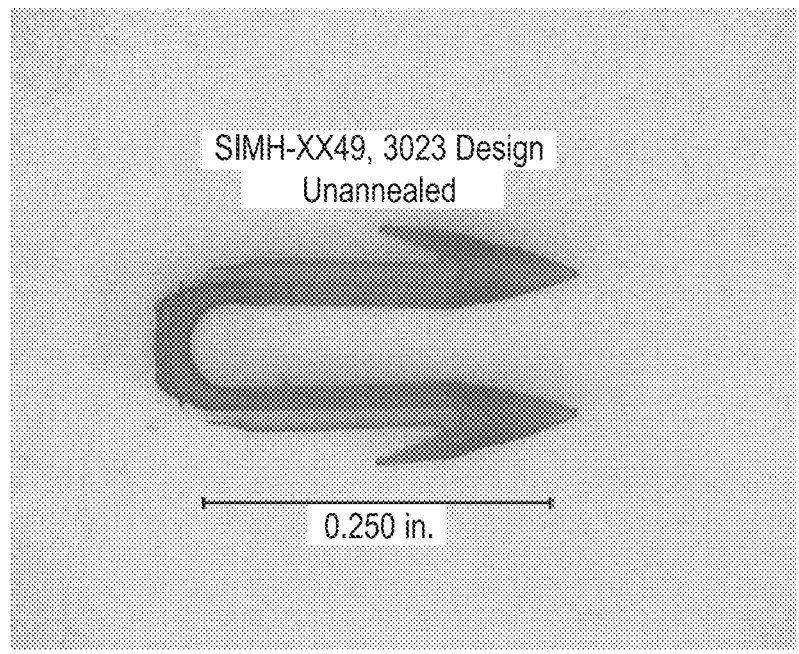
FIG. 10 is a photographic image of an injection molded tack of Sample STR 10-3 prior to annealing made from the polymer composition of Example 7A having 20 weight percent 92/8 poly(p-dioxanone-co-glycolide).
Figure 11:
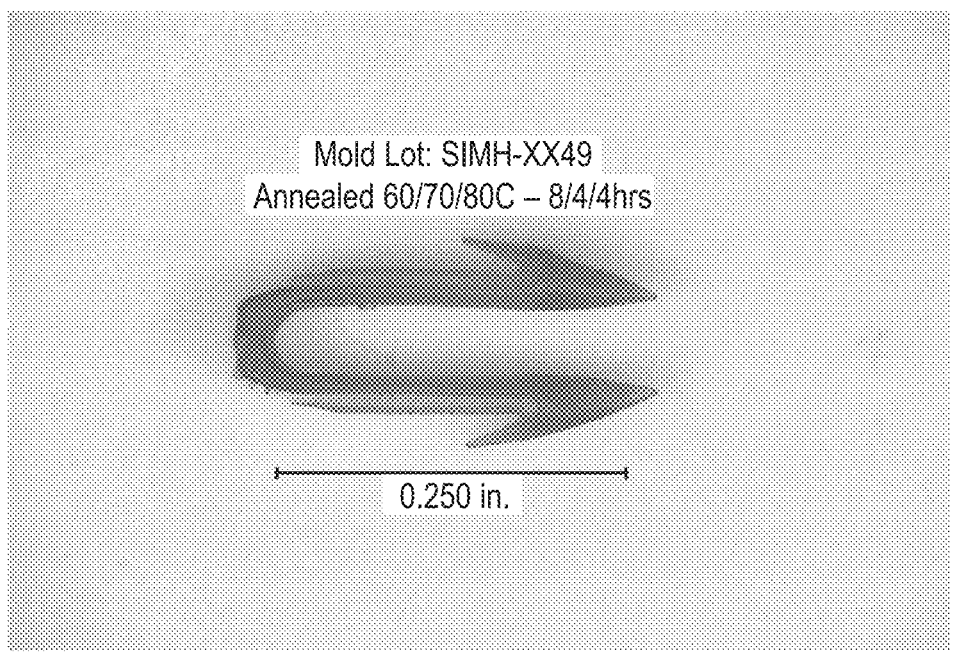
FIG. 11 is a photographic image of an injection molded tack of Sample STR 10-3 after annealing, made from the polymer composition of Example 7B having 20 weight percent 92/8 poly(p-dioxanone-co-glycolide), said injection molded tack exhibiting superior dimensional stability and an acceptable level of warping after annealing.
Figure 12A:
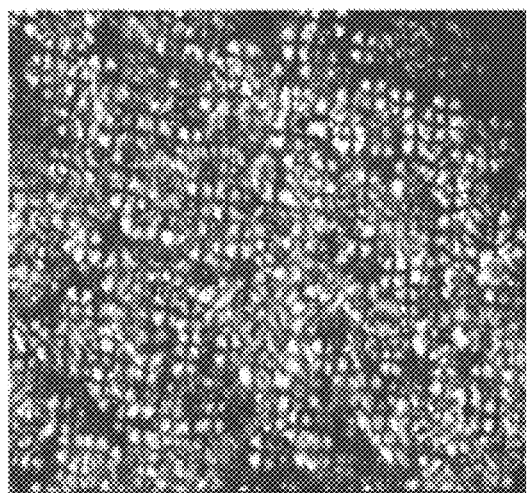
FIGS. 12A-12D show four Hot Stage Optical Microscopy images of copolymers in Examples 11A-11D, captured after 60 minutes of isothermal crystallization at 40° C.
Figure 12B:
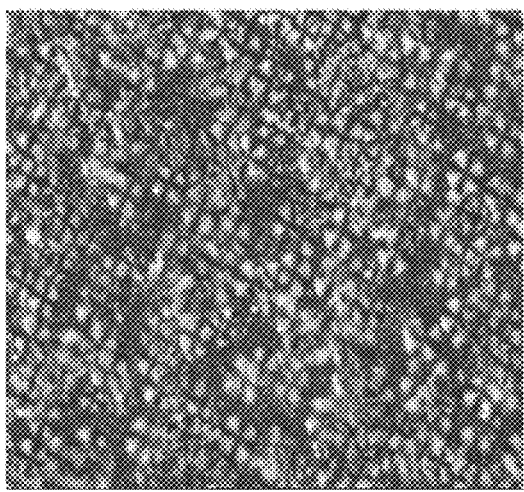
Figure 12C:
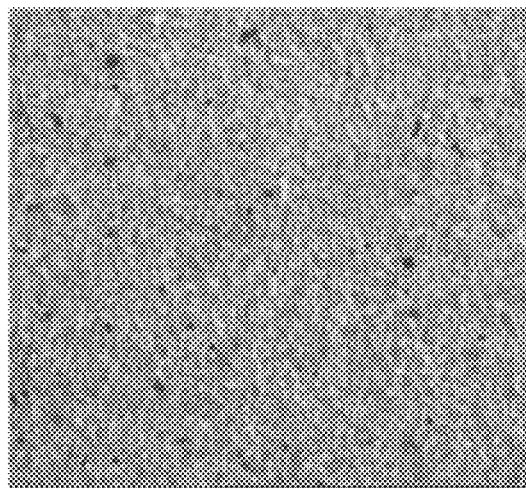
Figure 12D:
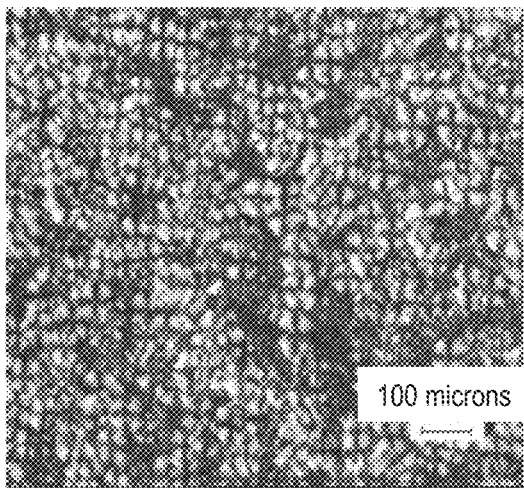

FIG. 10 is a photographic image of an injection molded tack of Sample STR 10-3 prior to annealing made from the polymer composition of Example 7A having 20 weight percent 92/8 poly(p-dioxanone-co-glycolide) copolymer; FIG. 11 is a photographic image of an injection molded tack of Sample STR 10-3 after annealing made from the polymer composition of Example 7B having 20 weight percent 92/8 poly(p-dioxanone-co-glycolide) copolymer; these injection molded tacks exhibited superior dimensional stability and an acceptable level of warping after annealing.

Returning to the data presented in Table 7, it is found that in the case of the annealed straps of Samples STR 10-3 to 10-5, two separate glass transition phenomena and two separate melting endotherms were observed. These corresponded to the 92/8 poly(p-dioxanone-co-glycolide) copolymer blend component and the lactide-based blend components. The observation of two glass transition temperatures is universally accepted supportive evidence of blend component immiscibility. This is in opposition to a blend of two or more materials in which the blend components are mutually soluble in each other leading to the observation of only one glass transition. All 92/8 PDO/Gly-based glass transition temperatures were well below room temperature between about −1° C. and about −7° C., while the glass transition temperatures associated with the lactide-rich-based blend components were well above room temperature between about 57° C. and about 59° C.

Two melting points were observed in the annealed injection molded articles made from the various blends shown in Table 7. The observation of two melting points is evidence that each blend component was crystallizable and did indeed crystallize during the annealing treatment. The annealed articles of the subject invention are semicrystalline in nature. All 92/8 92/8 PDO/Gly-based melting temperatures were between 101° C. and 102° C., while the melting temperatures associated with the lactide-rich-based blend component, 85/15 L/G, were observed to be between 146° C. and 149° C.

Example 11

Synthesis of Various 92/8
Poly(p-dioxanone-co-glycolide) Copolymers
Utilizing Specific Initiators Table 8 summarizes data from the synthesis of 92/8 (mole basis) poly(p-dioxanone-co-glycolide) copolymers (Examples 11A to 11E) utilizing specific initiators at the indicated ratios.

TABLE 8

Synthesis of 92/8 (Mole Basis) Poly(p-Dioxanone-Co-Glycolide) Copolymers

| Copolymer ID | DD/DEG molar ratio (%) | Monomer to initiators ratio | IV (dL/g) | $M_w$ (g/mole) |
|---|---|---|---|---|
| 11A | 100/0 | ~1,200:1 | 1.73 | 80,000 |
| 11B | 75/25 | ~1,000:1 | 1.77 | 73,000 |
| 11C | 50/50 | ~1,000:1 | 1.61 | 68,000 |
| 11D | 25/75 | ~1,000:1 | 1.55 | 55,000 |
| 11E | 0/100 | ~800:1 | 1.41 | 49,000 |

* IV, Inherent Viscosity, was conducted using hexafluoroisopropanol (HFIP) at a concentration of 0.1 g/dL, and a temperature of 25° C.

Outstanding crystallization properties of Copolymer 11C (50:50 DD:DEG ratio) were discovered when studied under isothermal crystallization conditions using hot-stage optical microscopy, HSOM. HSOM images of Copolymers 11A-11D are shown in FIGS. 12A to 12D. First, the nucleation rates for Copolymer 11C, observed at higher temperatures, were found slower than in Copolymer 11B (75/25 DD/DEG ratio), but increased rather abruptly when the crystallization temperature is lowered. When studied at a lower temperature range, a visual inspection of the copolymer's crystalline morphology indicated that, due to the extensive nucleation process, total crystal impingement occurred almost instantaneously (see FIG. 12C of the Copolymer 11C). It was discovered that the nucleation density of Copolymer 11C was extremely high compared to the balance of copolymers described in Table 8. While not intending to be bound by this theory, such a high degree of nucleation apparently controlled the crystal growth via an impingement process, even at very early stages of the process. Thus, the boundaries of developed structures approached each other, causing the crystals to stop growing. This produced, in turn, a large number of crystals with very small size. It was estimated that the average diameter of the crystals at the studied conditions (40° C. after 60 minutes) was about 8 microns. The balance of the copolymers described in Table 8 had a value significantly higher at about 70 microns.

The overall crystallization rates depend heavily on two factors: the concentration of growing spherulites with time (nucleation rate) and the rate of spherulitic growth. It is anticipated that these processes would have a measurable effect on calorimetric data. Differential Scanning calorimetry, DSC has several technical advantages including small sample size, an easy-to-handle apparatus, and more importantly, the ability to achieve a rapid thermal equilibrium, especially at high undercooling. Because of these characteristics, DSC has been one of the most convenient and popular methods in studying crystallization behavior of polymers using both, non-isothermal and isothermal methods.

DSC data generated on the copolymers of Example 11A to 11E during cooling from the melt support earlier evidence from HSOM, indicating clearly superb crystallization behavior of Copolymer 11C. A thermogram captured during the constant cooling rate (0.5° C./min) experiment for this copolymer is shown in FIG. 13. Several important parameters can be extracted from this figure. The high temperature slope of the peak represents the crystallization rate under given conditions. The area under the peak is proportional to overall crystallinity in the material. The temperature at the maximum peak indicates the location of the crystallization processes at the given cooling rate.

It is believed that the inventive concepts of this application may be practiced in a variety of ways. Further examples of practice are provided below. Example 12 supports three categories of practice, Case I, Case II and Case III.

Example 12

Further Description of Various Embodiments of the Present Invention

A number of embodiments will be further described; these can be summarized in Table 9 below:

TABLE 9

A Further Description of Various Embodiments of the Present Invention

| Case | L/G Copolymer Present | L/G Copolymer Mixed Initiator | Poly(p-dioxanone) Present | Poly(p-dioxanone) Mixed Initiator | Polylactide* Present | Polylactide* Mixed Initiator | Poly(p-dioxanone-co-glycolide) Present | Poly(p-dioxanone-co-glycolide) Mixed Initiator |
|---|---|---|---|---|---|---|---|---|
| I | X | YES | X | NO | | | | |
| IIA | X | NO | | | | | X | YES |
| IIB | | | | | X | NO | X | YES |
| III | X | YES | | | | | X | YES |
| IV | X | YES | | | | | X | NO |

*Crystallizable polylactides including poly(L(−)-lactide, poly(D(+)-lactide, and mixtures of the two.

While the following examples demonstrate certain embodiments of the invention, they are not to be interpreted as limiting the scope of the invention, but rather as contributing to a complete description of the invention.

Case I
The Lactide/Glycolide Copolymer Component is Synthesized using Mixed Initiators; the Second Component is Poly(p-dioxanone)

It is to be understood that in one embodiment a lactide/glycolide copolymer synthesized using a mixture of monofunctional and di-functional initiators may be substituted for the lactide/glycolide copolymer blend component of the parent invention, provided that the composition of the copolymer comprises about 95 mole percent to about 70 mole percent polymerized lactide and about 5 mole percent to about 30 mole percent polymerized glycolide. To be clear, polylactide homopolymer is not claimed in this embodiment.

Of particular utility are those lactide/glycolide copolymers synthesized using a mixture of mono- and di-functional initiators, wherein the molar ratio of mono-functional to di-functional initiator is from about 10:90 to about 90:10. Of further particular advantage is when the lactide/glycolide copolymer blend component in the inventive blend is synthesized using a combination of initiators selected from the group: 1-hexanol, 1-heptanol, 1-octanol, 1-nonanol, 1-decanol, dodecanol, ethylene glycol, diethylene glycol, and triethylene glycol, 1,4-butanediol, 1,6-hexanediol, 1,8-octanediol, 1,10-decanediol, and 1,12-dodecanediol.

The 85/15 Lactide/Glycolide Copolymer Component is Made Using Mixed Initiators, Dodecanol and Diethylene Glycol, and the Second Blend Component is Poly(p-dioxanone)

Eighty kilograms of pellets or ground material of a lactide/glycolide copolymer, having a composition of approximately 85 mole percent polymerized lactide and 15 mole percent polymerized glycolide, having a weight average molecular weight of approximately 75,000 Daltons and synthesized using a mixture of dodecanol and diethylene glycol as the initiator system in the ratio of 75/25, is dry mixed with twenty kilograms of pellets or ground material of poly(p-dioxanone) having a weight average molecular weight of approximately 80,000 Daltons. This mixture is melt compounded to result in a blend of 85/15 lactide/glycolide copolymer with poly(p-dioxanone) with the poly(p-dioxanone) component representing about 20 weight percent of the final blend. The weight average molecular weight of this final blend is approximately 72,000 Daltons.

It should be clear to one having ordinary skill in the art that similar blends differing in composition can be made in like manner.

Case II

The Poly(p-dioxanone) is Substituted with Poly(p-dioxanone-co-glycolide) Copolymer Made by Mixed Initiators; the Other Blend Component is Either Lactide/Glycolide Copolymer [Case IIA] Made by Single Initiator, or Polylactide [Case IIB] Made by Single Initiator In this embodiment a poly(p-dioxanone-co-glycolide) synthesized using a mixture of mono-functional and di-functional initiators will be substituted for the poly(p-dioxanone) blend component of the parent patent application. Of particular utility are those poly(p-dioxanone-co-glycolide) copolymers having a composition wherein the mole percent of polymerized p-dioxanone is from about 90 to about 95, and the mole percent of polymerized glycolide is from about 5 mole percent to about 10 mole percent. This poly(p-dioxanone-co-glycolide) copolymer is made utilizing a mono-functional polymerization initiator and a di-functional polymerization initiator at a mole ratio of mono-functional initiator to di-functional initiator of from 40/60 to 60/40.

Case IIA

The Poly(p-dioxanone) is Substituted with a 92/8 Poly(p-dioxanone-co-glycolide) Copolymer Made by Mixed Initiators; the Other Blend Component is 85/15 Lactide/Glycolide Copolymer Made by a Single Initiator, Dodecanol Eighty kilograms of pellets or ground material of a lactide/glycolide copolymer, having a composition of approximately 85 mole percent polymerized lactide and 15 mole percent polymerized glycolide, having a weight average molecular weight of approximately 75,000 Daltons and synthesized using dodecanol as the initiator, is dry mixed with twenty kilograms of pellets or ground material of 92/8 poly(p-dioxanone-co-glycolide) copolymer. This latter copolymer is synthesized using a mixture of dodecanol and diethylene glycol as the initiator system in the ratio of 50/50, and has a weight average molecular weight of approximately 80,000 Daltons. This mixture is melt compounded to result in a blend of 85/15 lactide/glycolide copolymer with 92/8 poly(p-dioxanone-co-glycolide) with the latter component representing about 20 weight percent of the final blend. The weight average molecular weight of this final blend is approximately 72,000 Daltons.

It should be clear to one having ordinary skill in the art that similar blends differing in composition can be made in like manner.

Case IIB

The Poly(p-dioxanone) is Substituted with 92/8 Poly(p-dioxanone-co-glycolide) Copolymer Made by Mixed Initiators; the Other Blend Component is Poly(L(−)-Lactide) Made by a Single Initiator, Dodecanol Eighty kilograms of pellets or ground material of a poly(L(−)-lactide) homopolymer having a weight average molecular weight of approximately 75,000 Daltons and synthesized using dodecanol as the initiator, is dry mixed with twenty kilograms of pellets or ground material of 92/8 poly(p-dioxanone-co-glycolide) copolymer. This latter copolymer is synthesized using a mixture of dodecanol and diethylene glycol as the initiator system in the ratio of 50/50, and has a weight average molecular weight of approximately 80,000 Daltons. This mixture is melt compounded to result in a blend of poly(L(−)-lactide) with 92/8 poly(p-dioxanone-co-glycolide) with the latter component representing about 20 weight percent of the final blend. The weight average molecular weight of this final blend is approximately 72,000 Daltons.

It should be clear to one having ordinary skill in the art that similar blends differing in composition can be made in like manner.

Case III

Both Blend Components, Lactide/Glycolide Copolymer and Poly(p-dioxanone-co-glycolide) Copolymer, are Made using Mixed Initiators In this particular embodiment, both blend components are made using mixed initiator systems. That is, a lactide/glycolide copolymer synthesized using a mixture of mono-functional and di-functional initiators is substituted for the lactide/glycolide copolymer blend component of the parent invention, provided that the composition of the copolymer comprises about 95 mole percent to about 70 mole percent polymerized lactide and about 5 mole percent to about 30 mole percent polymerized glycolide; and a poly(p-dioxanone-co-glycolide) synthesized using a mixture of mono-functional and di-functional initiators is substituted for the poly(p-dioxanone) blend component of the parent patent application. Of particular utility are those poly(p-dioxanone-co-glycolide) copolymers having a composition wherein the mole percent of polymerized p-dioxanone is from about 90 to about 95, and the mole percent of polymerized glycolide is from about 5 mole percent to about 10 mole percent. This poly(p-dioxanone-co-glycolide) copolymer is made utilizing a mono-functional polymerization initiator and a di-functional polymerization initiator at a mole ratio of mono-functional initiator to di-functional initiator of from 40/60 to 60/40. To be clear, polylactide homopolymer is not indicated in this embodiment.

The 85/15 Lactide/Glycolide Copolymer Component is Made using Mixed Initiators, Dodecanol and Diethylene Glycol; the Second Blend Component is 92/8 Poly(p-dioxanone-co-glycolide) Copolymer also Made by Mixed Initiators, Dodecanol and Diethylene Glycol Eighty kilograms of pellets or ground material of a lactide/glycolide copolymer, having a composition of approximately 85 mole percent polymerized lactide and 15 mole percent polymerized glycolide, having a weight average molecular weight of approximately 75,000 Daltons and synthesized using a mixture of dodecanol and diethylene glycol as the initiator system in the ratio of 75/25, is dry mixed with twenty kilograms of pellets or ground material of 92/8 poly(p-dioxanone-co-glycolide) copolymer. This latter copolymer is synthesized using a mixture of dodecanol and diethylene glycol as the initiator system in the ratio of 50/50, and has a weight average molecular weight of approximately 80,000 Daltons. This mixture is melt compounded to result in a blend of 85/15 poly(L(−)-lactide-co-glycolide) with 92/8 poly(p-dioxanone-co-glycolide) with the latter component representing about 20 weight percent of the final blend. The weight average molecular weight of this final blend is approximately 72,000 Daltons.

It should be clear to one having ordinary skill in the art that similar blends differing in composition can be made in like manner.

Case IV
The Lactide/Glycolide Copolymer is Made using Mixed Initiators and the Second Blend Component is Poly(p-dioxanone-co-glycolide) Copolymer Made using a Single Initiator Type (Mono-Functional or Di-Functional)

In this embodiment a lactide/glycolide copolymer synthesized using a mixture of mono-functional and di-functional initiators may be substituted for the lactide/glycolide copolymer blend component of the parent invention, provided that the composition of the copolymer comprises about 95 mole percent to about 70 mole percent polymerized lactide and about 5 mole percent to about 30 mole percent polymerized glycolide. To be clear, polylactide homopolymer is not indicated in this embodiment. The second blend component in this embodiment is a poly(p-dioxanone-co-glycolide) synthesized using either a mono-functional or a di-functional initiator, not a mixture of the two. Of particular utility are those poly(p-dioxanone-co-glycolide) copolymers having a composition wherein the mole percent of polymerized p-dioxanone is from about 90 to about 95, and the mole percent of polymerized glycolide is from about 5 mole percent to about 10 mole percent.

The 85/15 Lactide/Glycolide Copolymer Component is Made using Mixed Initiators, Dodecanol and Diethylene Glycol; the Second Blend Component is 92/8 Poly(p-dioxanone-co-glycolide) Copolymer Made by a Single Initiators Type, Dodecanol Eighty kilograms of pellets or ground material of a lactide/glycolide copolymer, having a composition of approximately 85 mole percent polymerized lactide and 15 mole percent polymerized glycolide, having a weight average molecular weight of approximately 75,000 Daltons and synthesized using a mixture of dodecanol and diethylene glycol as the initiator system in the ratio of 75/25, is dry mixed with twenty kilograms of pellets or ground material of 92/8 poly(p-dioxanone-co-glycolide) copolymer. This latter copolymer is synthesized using dodecanol (only) as the initiator system and has a weight average molecular weight of approximately 80,000 Daltons. This mixture is melt compounded to result in a blend of 85/15 poly(L(−)-lactide-co-glycolide) with 92/8 poly(p-dioxanone-co-glycolide) with the latter component representing about 20 weight percent of the final blend. The weight average molecular weight of this final blend is approximately 72,000 Daltons.

It should be clear to one having ordinary skill in the art that similar blends differing in composition can be made in like manner.

The novel polymer blends of the present invention having one or more blend components synthesized using mixed initiators have many advantages. The advantages of the present invention are numerous. They include the following:

Increased dimensional stability due to the development of higher crystallinity levels in fabricated implantable parts;

Lower injection molding cycle times due to faster polymer nucleation, and faster crystallization;

The achievement of higher stiffness in fabricated implantable parts by virtue of higher crystallinity levels and/or lowering the level of the second blend component [poly (p-dioxanone) or poly(p-dioxanone-co-glycolide)]; this characteristic is particularly advantageous in medical devices that must penetrate tough bodily tissues; and, Providing a wide range of retention of mechanical properties post-implantation; for instance, if desired, a fast crystallizing poly(p-dioxanone-co-glycolide) made with mixed initiators may be substituted for poly(p-dioxanone) allowing faster hydrolysis due to the presence of polymerized glycolide moieties, leading to a rapid loss of mechanical properties post-implantation; likewise, if desired, a longer retention of mechanical properties can be achieved lowering the amount of the second blend component while still providing good dimensional stability in fabricated parts by virtue of the development of higher crystallinity levels.

Example 13

Calculating the Minimum Weight Percent of Poly(p-dioxanone) Homopolymer or Poly(p-dioxanone-co-glycolide) Copolymer in the Present Inventive Blends For Case I embodiments (see Table 9), a lactide-rich lactide-co-glycolide copolymer made with mixed initiators is one of the blend components; the other blend component is poly(p-dioxanone). The minimum weight percent of the poly (p-dioxanone) in the blend of the present invention can be calculated using the equation found below.

$$\text{Weight Percent Poly}(p\text{-dioxanone}) = (215.6212/\text{Mole Percent Polymerized Lactide})^{2.7027}$$

For example, when the composition of the lactide-rich lactide-co-glycolide copolymer made with mixed initiators is 82/18 (on a mole basis), the minimum weight percent of poly(p-dioxanone) in the blend is calculated to be 13.6 percent and the maximum amount was 50. Likewise, if the composition of the lactide-co-glycolide copolymer is 86/14 (on a mole basis), the minimum weight percent of poly(p-dioxanone) in the blend is calculated to be 12.0 percent and the maximum amount was 50. Table 10 contains a chart of the range of poly(p-dioxanone) expressed as minimum and maximum weight percent, in this Case I embodiment of the blend of the subject invention.

For Case II embodiments (see Table 9) one of the blend components is a polylactide homopolymer made with a single initiator type (Case IIB), or a lactide-rich lactide-co-glycolide copolymer made with a single initiator type (Case IIA); the other blend component is poly(p-dioxanone-co-glycolide)

copolymer made with mixed initiators. The minimum weight percent of poly(p-dioxanone-co-glycolide) copolymer made with mixed imitators in the blend of the present invention can be calculated using the equation found below.

Weight Percent Poly(*p*-dioxanone-co-glycolide)= (215.6212/Mole Percent Polymerized Lactide)$^{2.7027}$ For example, when the composition of the lactide-rich lactide-co-glycolide copolymer made with a single initiator type is 82/18 (on a mole basis), the minimum weight percent of poly(p-dioxanone) in the blend is calculated to be 13.6 percent and the maximum amount was 50. Likewise, if the composition of the lactide-rich lactide-co-glycolide copolymer made with a single initiator type is 86/14 (on a mole basis), the minimum weight percent of poly(p-dioxanone) in the blend is calculated to be 12.0 percent and the maximum amount was 50. Table 10 contains a chart of the range of poly(p-dioxanone-co-glycolide) expressed as minimum and maximum weight percent, in this Case II embodiment of the blend of the subject invention.

For Case III embodiments (see Table 9), a lactide-rich, lactide-co-glycolide copolymer made with mixed initiators is one of the blend components; the other blend component is poly(p-dioxanone-co-glycolide) also made with mixed initiators. The minimum weight percent of the poly(p-dioxanone-co-glycolide) in the blend of the present invention can be calculated using the equation found below.

Weight Percent Poly(*p*-dioxanone-co-glycolide)= (215.6212/Mole Percent Polymerized Lactide)$^{2.7027}$ For example, when the composition of the lactide-rich lactide-co-glycolide copolymer made with mixed initiators is 82/18 (on a mole basis), the minimum weight percent of poly(p-dioxanone-co-glycolide) copolymer made with mixed initiators in the blend is calculated to be 13.6 percent and the maximum amount was 50. Likewise, if the composition of the lactide-co-glycolide copolymer is 86/14 (on a mole basis), the minimum weight percent of poly(p-dioxanone-co-glycolide) copolymer made with mixed initiators in the blend is calculated to be 12.0 percent and the maximum amount was 50. Table 10 contains a chart of the range of poly(p-dioxanone-co-glycolide) expressed as minimum and maximum weight percent, in this Case III embodiment of the blend of the subject invention.

For Case IV embodiments (see Table 9), a lactide-rich, lactide-co-glycolide copolymer made with mixed initiators is one of the blend components; the other blend component is poly(p-dioxanone-co-glycolide) also made with a single initiator. The minimum weight percent of the poly(p-dioxanone-co-glycolide) in the blend of the present invention can be calculated using the equation found below.

Weight Percent Poly(*p*-dioxanone-co-glycolide)= (215.6212/Mole Percent Polymerized Lactide)$^{2.7027}$ For example, when the composition of the lactide-rich lactide-co-glycolide copolymer made with mixed initiators is 82/18 (on a mole basis), the minimum weight percent of poly(p-dioxanone-co-glycolide) copolymer made with a single initiator in the blend is calculated to be 13.6 percent and the maximum amount was 50. Likewise, if the composition of the lactide-co-glycolide copolymer is 86/14 (on a mole basis), the minimum weight percent of poly(p-dioxanone-co-glycolide) copolymer made with a single initiator in the blend is calculated to be 12.0 percent and the maximum amount was 50. Table 10 contains a chart of the range of poly(p-dioxanone-co-glycolide) expressed as minimum and maximum weight percent, in this Case IV embodiment of the blend of the subject invention.

TABLE 10

Inventive Blend Compositions based on the Various Embodiments of the Present Invention Described in Table 9

| Mole Percent Polymerized Lactide in the Polylactide Homopolymer or Lactide-Based (Co)Polymer | Minimum Weight Percent Poly(p-dioxanone) Homopolymer or Poly(p-dioxanone-co-glycolide) Copolymer | Maximum Weight Percent Poly(p-dioxanone) Homopolymer or Poly(p-dioxanone-co-glycolide) Copolymer |
|---|---|---|
| 100 | 8.0 | 50 |
| 99 | 8.2 | 50 |
| 98 | 8.4 | 50 |
| 97 | 8.7 | 50 |
| 96 | 8.9 | 50 |
| 95 | 9.2 | 50 |
| 94 | 9.4 | 50 |
| 93 | 9.7 | 50 |
| 92 | 10.0 | 50 |
| 91 | 10.3 | 50 |
| 90 | 10.6 | 50 |
| 89 | 10.9 | 50 |
| 88 | 11.3 | 50 |
| 87 | 11.6 | 50 |
| 86 | 12.0 | 50 |
| 85 | 12.4 | 50 |
| 84 | 12.8 | 50 |
| 83 | 13.2 | 50 |
| 82 | 13.6 | 50 |
| 81 | 14.1 | 50 |
| 80 | 14.6 | 50 |
| 79 | 15.1 | 50 |
| 78 | 15.6 | 50 |
| 77 | 16.2 | 50 |
| 76 | 16.7 | 50 |
| 75 | 17.4 | 50 |
| 74 | 18.0 | 50 |
| 73 | 18.7 | 50 |
| 72 | 19.4 | 50 |
| 71 | 20.1 | 50 |
| 70 | 20.9 | 50 |

Although this invention has been shown and described with respect to detailed embodiments thereof, it will be understood by those skilled in the art that various changes in form and detail thereof may be made without departing from the spirit and scope of the claimed invention. It will be understood that the embodiments described herein are merely exemplary and that a person skilled in the art may make many variations and modifications, including but not limited to those discussed hereinabove, without departing from the spirit and scope of the present invention. All such variations and modifications are intended to be included within the scope of the present invention.

We claim:

1. An absorbable polymer blend, comprising:
   at least 50 weight percent of a first absorbable polymer, the first polymer comprising a lactide-rich polymer comprising about 95 mole percent to about 70 mole percent polymerized lactide and about 5 mole percent to about 30 mole percent polymerized glycolide, wherein the first absorbable polymer is synthesized using a mixture of mono- and di-functional initiators, and wherein the molar ratio of mono-functional to di-functional initiator is from about 10:90 to about 90:10; and,
   a second absorbable polymer, the second polymer comprising poly(p-dioxanone),
   wherein the maximum weight percent of poly(p-dioxanone) in the blend is 50 weight percent and the minimum weight percent of poly(p-dioxanone) in the blend is sufficient such that the polymer blend effectively provides dimensional stability to a manufactured article.

2. A medical device, comprising the absorbable polymer blend of claim 1.

3. A method of manufacturing a medical device, comprising the steps of:
providing the polymer blend of claim 1; and,
processing said blend into a medical device.

4. The absorbable polymer blend of claim 1,
wherein the minimum weight percent of poly(p-dioxanone) in the blend depends upon the molar amount of polymerized lactide in the lactide-rich polymer and is calculated by the expression:

Weight Percent Poly($p$-dioxanone)=(215.6212/Mole Percent Polymerized Lactide)$^{2.7027}$ when the lactide-rich polymer is made utilizing a mixture of mono- and di-functional initiators.

5. An absorbable polymer blend, comprising:
at least 50 weight percent of a first absorbable polymer, the first polymer a lactide-rich polymer comprising about 100 mole percent to about 70 mole percent polymerized lactide and about 0 mole percent to about 30 mole percent polymerized glycolide; and,
a second polymer comprising a poly(p-dioxanone-co-glycolide) copolymer, wherein the mole percent of polymerized p-dioxanone is from about 90 mole percent to about 95 mole percent, the mole percent of polymerized glycolide is from about 5 mole percent to about 10 mole percent, and wherein the copolymer is made utilizing a mono-functional polymerization initiator and a di-functional polymerization initiator at a mole ratio of mono-functional initiator to di-functional initiator of from about 40/60 to about 60/40,
wherein the maximum weight percent of poly(p-dioxanone-co-glycolide) copolymer in the blend is 50 weight percent and the minimum weight percent of poly(p-dioxanone-co-glycolide) copolymer in the blend is sufficient such that the polymer blend effectively provides dimensional stability to a manufactured article.

6. A medical device, comprising the absorbable polymer blend of claim 5.

7. A method of manufacturing a medical device, comprising the steps of:
providing the polymer blend of claim 5; and,
processing said blend into a medical device.

8. The absorbable polymer blend of claim 5,
wherein the minimum weight percent of poly(p-dioxanone-co-glycolide) in the blend depends upon the molar amount of polymerized lactide in the lactide-rich polymer and is calculated by the expression:

Weight Percent Poly($p$-dioxanone-co-glycolide)= (215.6212/Mole Percent Polymerized Lactide)$^{2.7027}$ when the lactide-rich polymer is made by a single initiator type and the poly(p-dioxanone-co-glycolide) is made by utilizing a mixture of mono- and di-functional initiators.

9. An absorbable polymer blend, comprising:
at least 50 weight percent of a first absorbable polymer, the first polymer comprising a lactide-rich polymer comprising about 95 mole percent to about 70 mole percent polymerized lactide and about 5 mole percent to about 30 mole percent polymerized glycolide, said first absorbable polymer is made utilizing a mono-functional polymerization initiator and a di-functional polymerization initiator at a mole ratio of mono-functional initiator to di-functional initiator of from about 10/90 to about 90/10; and,
a second polymer comprising a poly(p-dioxanone-co-glycolide) copolymer, wherein the mole percent of polymerized p-dioxanone is from about 90 mole percent to about 95 mole percent, the mole percent of polymerized glycolide is from about 5 mole percent to about 10 mole percent, and wherein the copolymer is made utilizing a mono-functional polymerization initiator and a di-functional polymerization initiator at a mole ratio of mono-functional initiator to di-functional initiator of from about 40/60 to about 60/40,
wherein the maximum weight percent of poly(p-dioxanone-co-glycolide) copolymer in the blend is 50 weight percent and the minimum weight percent of poly(p-dioxanone-co-glycolide) copolymer in the blend is sufficient such that the polymer blend effectively provides dimensional stability to a manufactured article.

10. A medical device, comprising the absorbable polymer blend of claim 9.

11. A method of manufacturing a medical device, comprising the steps of:
providing the polymer blend of claim 9; and,
processing said blend into a medical device.

12. The absorbable polymer blend of claim 9,
wherein the minimum weight percent of poly(p-dioxanone-co-glycolide) in the blend depends upon the molar amount of polymerized lactide in the lactide-rich polymer and is calculated by the expression:

Weight Percent Poly($p$-dioxanone-co-glycolide)= (215.6212/Mole Percent Polymerized Lactide)$^{2.7027}$ when the lactide-rich polymer and the poly(p-dioxanone-co-glycolide) are made by utilizing a mixture of mono- and di-functional initiators.

13. An absorbable polymer blend, comprising:
at least 50 weight percent of a first absorbable polymer comprising a lactide-rich polymer comprising about 95 mole percent to about 70 mole percent polymerized lactide and about 5 mole percent to about 30 mole percent polymerized glycolide, wherein the first absorbable polymer is synthesized using a mixture of mono- and di-functional initiators and the molar ratio of mono-functional to di-functional initiator is from about 10:90 to about 90:10; and,
a second polymer comprising poly(p-dioxanone-co-glycolide) copolymer, wherein the mole percent of polymerized p-dioxanone is from about 90 to about 99, the mole percent of polymerized glycolide is from about 1 mole percent to about 10 mole percent,
wherein the maximum weight percent of poly(p-dioxanone-co-glycolide) copolymer in the blend is 50 weight percent and the minimum weight percent of poly(p-dioxanone-co-glycolide) copolymer in the blend is sufficient such that the polymer blend effectively provides dimensional stability to a manufactured article.

14. A medical device, comprising the absorbable polymer blend of claim 13.

15. A method of manufacturing a medical device, comprising the steps of:
providing the polymer blend of claim 13; and,
processing said blend into a medical device.

16. The absorbable polymer blend of claim 13,
wherein the minimum weight percent of poly(p-dioxanone-co-glycolide) in the blend depends upon the molar amount of polymerized lactide in the lactide-rich polymer and is calculated by the expression:

$$\text{Weight Percent Poly}(p\text{-dioxanone-co-glycolide}) = (215.6212/\text{Mole Percent Polymerized Lactide})^{2.7027}$$

when the lactide-rich polymer is made by utilizing a mixture of mono- and di-functional initiators and the poly(p-dioxanone-co-glycolide) is made using a single initiator.

* * * * *